US012576195B2

(12) United States Patent
Friederichs et al.

(10) Patent No.: US 12,576,195 B2
(45) Date of Patent: Mar. 17, 2026

(54) MEDICAMENT PREPARATION DEVICES, METHODS, AND SYSTEMS

(71) Applicant: NxStage Medical, Inc., Lawrence, MA (US)

(72) Inventors: Goetz Friederichs, Beverly, MA (US); Gregory Yantz, Boxford, MA (US)

(73) Assignee: NxStage Medical, Inc., Lawrence, MA (US)

( * ) Notice: Subject to any disclaimer, the term of this patent is extended or adjusted under 35 U.S.C. 154(b) by 1045 days.

(21) Appl. No.: 17/505,288

(22) Filed: Oct. 19, 2021

(65) Prior Publication Data

US 2022/0126005 A1 Apr. 28, 2022

Related U.S. Application Data

(60) Provisional application No. 63/104,899, filed on Oct. 23, 2020.

(51) Int. Cl.
　　*A61M 1/28*　　　(2006.01)
　　*A61M 1/14*　　　(2006.01)
　　　　　　(Continued)

(52) U.S. Cl.
　　CPC ........ *A61M 1/1656* (2013.01); *A61M 1/1524* (2022.05); *A61M 1/154* (2022.05);
　　　　　　(Continued)

(58) Field of Classification Search
　　CPC .... A61M 1/1524; A61M 1/154; A61M 1/155; A61M 1/1565; A61M 1/159;
　　　　　　(Continued)

(56) References Cited

U.S. PATENT DOCUMENTS

| 4,136,708 A | 1/1979 | Cosentino et al. |
| 5,511,875 A | 4/1996 | Jonsson et al. |

(Continued)

FOREIGN PATENT DOCUMENTS

| EP | 1312386 A2 | 5/2003 |
| JP | 2009533092 A | 9/2009 |

(Continued)

OTHER PUBLICATIONS

International Search Report and Written Opinion mailed Aug. 1, 2022 for International Patent Application No. PCT/US2022/022591.

(Continued)

*Primary Examiner* — John Kim
(74) *Attorney, Agent, or Firm* — Potomac Law Group, PLLC

(57) ABSTRACT

A proportioning device includes a proportioning machine with a temperature-compensating conductivity sensor, a controller, and pump actuator. A fluid circuit is engageable with the pump actuator, has connections for a source of water and one or more medicament concentrates, and includes a mixing container. The controller is configured to mix contents of the mixing container at a first time and to sample fluid from the mixing container, to pass the samples from the mixing container through the temperature-compensating conductivity sensor at different points in time as the fluid flows from the mixing container. The controller is further configured to mix contents of the mixing container a second time if the conductivities differ by a predefined magnitude.

10 Claims, 13 Drawing Sheets

(51) Int. Cl.

| | |
|---|---|
| *A61M 1/16* | (2006.01) |
| *A61M 60/279* | (2021.01) |
| *A61M 60/37* | (2021.01) |
| *B01F 23/00* | (2022.01) |
| *G05D 21/02* | (2006.01) |

(52) U.S. Cl.

CPC .......... *A61M 1/155* (2022.05); *A61M 1/1565* (2022.05); *A61M 1/159* (2022.05); *A61M 1/1601* (2014.02); *A61M 1/28* (2013.01); *A61M 1/282* (2014.02); *A61M 1/287* (2013.01); *A61M 60/279* (2021.01); *A61M 60/37* (2021.01); *B01F 23/00* (2022.01); *G05D 21/02* (2013.01); *A61M 2205/3317* (2013.01); *A61M 2205/3331* (2013.01); *A61M 2205/3355* (2013.01); *A61M 2205/3368* (2013.01); *A61M 2205/3372* (2013.01)

(58) Field of Classification Search

CPC .... A61M 1/1601; A61M 1/1656; A61M 1/28; A61M 1/282; A61M 1/287; A61M 60/279; A61M 60/37; A61M 2205/3355; A61M 2205/3317; A61M 2205/3331; A61M 2205/3368; A61M 2205/3372; B01F 23/00; G05D 21/02

See application file for complete search history.

(56) References Cited

U.S. PATENT DOCUMENTS

| | | | |
|---|---|---|---|
| 5,591,344 | A | 1/1997 | Kenley et al. |
| 6,280,632 | B1 | 8/2001 | Polaschegg |
| 8,191,339 | B2 | 6/2012 | Tribble et al. |
| 9,867,929 | B2 | 1/2018 | Searle et al. |
| 11,207,454 | B2 | 12/2021 | Wyeth et al. |
| 2008/0230450 | A1 | 9/2008 | Burbank et al. |
| 2013/0168316 | A1 | 7/2013 | Noguchi et al. |
| 2015/0005699 | A1 | 1/2015 | Burbank et al. |
| 2017/0290970 | A1 | 10/2017 | Friederichs et al. |
| 2017/0319768 | A1 | 11/2017 | Szpara et al. |
| 2018/0104400 | A1 | 4/2018 | Burbank et al. |
| 2019/0151526 | A1 | 5/2019 | Wieslander et al. |
| 2019/0201607 | A1 | 7/2019 | Öberg |
| 2019/0217000 | A1 | 7/2019 | Burbank et al. |
| 2019/0262522 | A1 | 8/2019 | Wyeth et al. |
| 2019/0262524 | A1 | 8/2019 | Wyeth et al. |
| 2019/0262526 | A1 | 8/2019 | Wyeth et al. |
| 2019/0275226 | A1 | 9/2019 | Burbank et al. |
| 2020/0009308 | A1 | 1/2020 | Friederichs et al. |
| 2020/0016317 | A1 | 1/2020 | Kelly et al. |
| 2020/0171230 | A1 | 6/2020 | Brugger et al. |
| 2020/0254167 | A1* | 8/2020 | Rohde .................. A61M 1/284 |
| 2020/0390954 | A1 | 12/2020 | Rovatti et al. |
| 2022/0126005 | A1 | 4/2022 | Friederichs et al. |

FOREIGN PATENT DOCUMENTS

| | | |
|---|---|---|
| JP | 2018134444 A | 8/2018 |
| WO | 2013141896 A1 | 9/2013 |
| WO | 2020237033 A1 | 11/2020 |
| WO | 2021101899 A1 | 5/2021 |
| WO | 2022086922 A2 | 4/2022 |
| WO | 2022204253 A1 | 9/2022 |

OTHER PUBLICATIONS

International Search Report and Written Opinion mailed Aug. 30, 2022 for International Patent Application No. PCT/US2022/020583.

International Search Report and Written Opinion mailed Sep. 9, 2022 for International Application No. PCT/US2022/021955.

Extended European Search Report dated Jul. 8, 2024 for European Patent Application No. 22772141.2.

Partial Supplementary European Search Report dated Jul. 4, 2024 for European Patent Application No. 22772033.1.

Gotch et al., "Mechanisms determining the ratio of conductivity clearance to urea clearance," Kidney International, vol. 66, Supplement 8, Jul. 2004, pp. S-3-S-24.

International Search Report and Written Opinion mailed Jun. 14, 2022 for International Patent Application No. PCT/US2022/021477.

International Search Report and Written Opinion mailed Jun. 24, 2022 for International Patent Application No. PCT/US2022/021501.

International Search Report and Written Opinion mailed Jun. 3, 2022 for International Patent Application No. PCT/US2022/020331.

Invitation to Pay Additional Fees mailed Apr. 29, 2022 for International Patent Application No. PCT/US2022/020583.

Invitation to Pay Additional Fees mailed Jun. 3, 2022 for International Patent Application No. PCT/US2022/022591.

Invitation to Pay Additional Fees mailed May 26, 2022 for International Patent Application No. PCT/US2022/021955.

Office Action (Communication Pursuant to Article 94(3) EPC) dated Apr. 19, 2024 for European Patent Application No. 21806560.5.

International Search Report and Written Opinion mailed Mar. 21, 2022 for International Patent Application No. PCT/US2021/055550.

Invitation to Pay Additional Fees mailed Jan. 31, 2022 for International Patent Application No. PCT/US2021/055550.

Extended European Search Report dated Feb. 4, 2025 for European Patent Application No. 22782109.7.

Office Action (Notice of Reasons for Refusal) mailed Apr. 22, 2025 for Japanese Patent Application No. 2023-523619.

* cited by examiner

MEDICAMENT PREPARATION DEVICES, METHODS, AND SYSTEMS

CROSS-REFERENCE TO RELATED APPLICATIONS

This application claims priority to and the benefit of U.S. Provisional Patent Application No. 63/104,899 filed Oct. 23, 2020, which is hereby incorporated by reference in its entirety.

BACKGROUND

The disclosed subject matter relates generally to devices, methods, systems, improvements, and components for preparing medicaments and making medicament available for use by a consumer, for example, a dialysis cycler.

Peritoneal dialysis is a mature technology that has been in use for many years. It is one of two common forms of dialysis, the other being hemodialysis, which uses an artificial membrane to directly cleanse the blood of a renal patient. Peritoneal dialysis employs the natural membrane of the peritoneum to permit the removal of excess water and toxins from the blood.

In peritoneal dialysis, sterile peritoneal dialysis fluid is infused into a patient's peritoneal cavity using a catheter that has been inserted through the abdominal wall. The fluid remains in the peritoneal cavity for a dwell period. Osmotic exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysis fluid is removed from the body cavity through the catheter.

SUMMARY

Methods, device, and systems for preparing medicaments such as, but not limited to, dialysis fluid are disclosed. In embodiments, medicament is prepared at a point of care (POC) automatically using a daily sterile disposable fluid circuit, one or more concentrates to make batches of medicament at the POC.

Embodiments of medicament preparation, devices, systems, and methods are described herein. The features, in some cases, relate to automated dialysis such as peritoneal dialysis, hemodialysis and others, and in particular to systems, methods, and devices that prepare peritoneal dialysis fluid in a safe and automated way at a point of care. The disclosed features may be applied to any kind of medicament system and are not limited to dialysis fluid.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
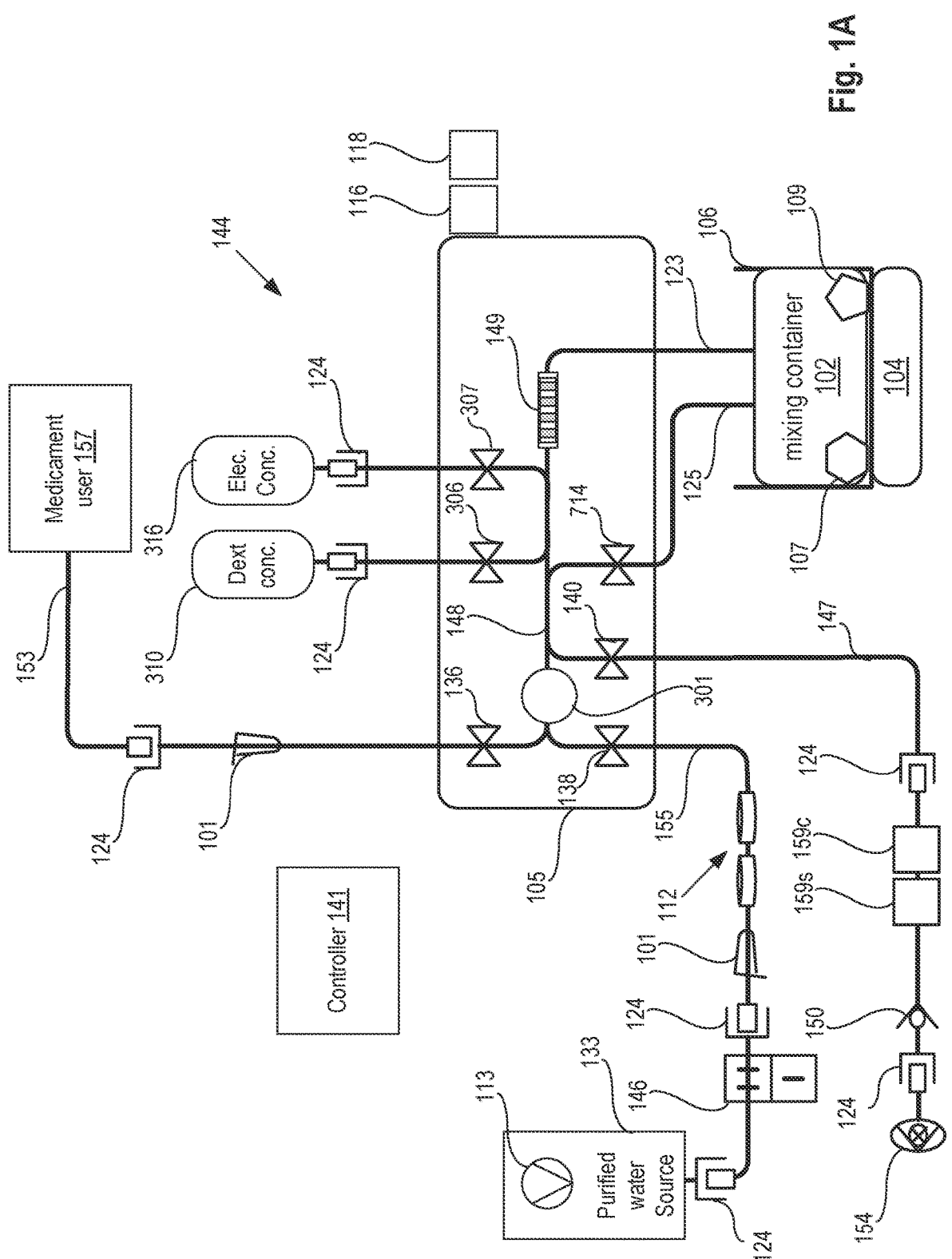
FIG. 1A shows a system for preparing a ready to use medicament from multiple media including concentrate and water according to embodiments of the disclosed subject matter.

Referring to FIG. 1A, a purified water source 133 with a water pump 113 supplies highly purified water through a connector 124 and then through a water line 155. The water line 155 has a non-reopenable clamp 146, another connector 124, a manual tube clamp 101, and a pair of redundant 0.2 micron sterilizing filters 112. A water inlet clamp 138, batch release clamp 136, and a conductivity sensor clamp 140 are controlled by a controller 141. Also, each of a first concentrate clamp 306 and a second concentrate clamp 307 control the flow of two concentrates, respectively. A mixing container line clamp 714 controls flow to and from a mixing container 102. The controller 141 controls the pinch clamps and a peristaltic pump 149 to make a batch of diluted concentrate in the mixing container 102. The mixing container 102 may be a vessel of any type, for example a bag. As a bag is held by a tub 106. The tub 106 is useful when the mixing container 102 may constitute a bag in order to provide support. A tub leak sensor 107 detects leaks into the tub 106 and a temperature sensor 109 detects the temperature of the fluid in the mixing container 102. A warmer 104 may be used if one does not exist in the medicament user 157. The medicament user 157 may be any type of a consuming device for example, a medical treatment device, for example, a peritoneal dialysis cycler or a hemodialysis cycler.

The peristaltic pump 149 moves fluid in a line 123 connected to the mixing container 102. The peristaltic pump 149 also moves fluid, at selected times, through the line 125 which may return the fluid to the mixing container 102 to stir its contents. Initially the purified water from the purified water source 133 is pumped by the water pump 113 with water inlet clamp 138 open and other clamps closed. The peristaltic pump 149 runs in a rightward direction to provide water to the mixing container 102. The water pump 113 and the peristaltic pump 149 may work in tandem with the controller controlling the speed of the water pump 113 and/or the peristaltic pump 149 to maintain a predefined pressure in a manifold line 148 responsively to the pressure indicated by a pressure sensor 301. The reason for pressure control is that the peristaltic pump 149 output is sensitive to inlet pressure changes. To mix the contents of the mixing container 102 the peristaltic pump 149 pumps fluid in a circular path through lines 123 and 125 with the all the clamps closed except for mixing container line clamp 714. The direction of the flow for mixing may be reversed such that the mixing may work in either way. Thus, the contents of the mixing container 102 are mixed by the flow circulating through the mixing container 102. A sample of the fluid in the mixing container 102 may be pumped through a drain conductivity line 147 which contains conductivity/temperature sensors 159c and 159s to determine a temperature-compensated conductivity of the diluted medicament. At this time, the batch release clamp 136 is open and the other clamps are closed. A pump, not shown, in a medicament user 157, may then draw fluid. The pump in the purified water source 133 or the peristaltic pump 149 may be feedback controlled, based on input from a pressure sensor 301, to maintain a predefined pressure at the pressure sensor 301. The medicament user 157 may be any type of treatment device or container that receives the mixed medicament from the mixing container 102.

Note that as used herein, the temperature-compensated conductivity (or simply conductivity) may be a value that is generated by the controller 141 by multiplying the measured conductivity with a value that represents the rate of change of concentration with temperature. In other embodiments, the controller 141 may calculate a concentration directly using a look-up table or formula.

Included in a disposable unit 144 are a medicament supply line 153, manifold line 148, water source line 155, drain conductivity line 147 and the mixing container 102. The disposable fluid circuit has permanent connection up to and including the connectors 124. A check valve 150 prevents back flow in the drain conductivity line 147. A pair of conductivity temperature sensors 159c and 159s. An attachment to drain or waste container is provided by a connector 154.

Mixed fluid is pumped through conductivity/temperature sensors 159c (control) and 159s (safety) and is determined to be mixed when two consecutive measurements are close within a range of each other. That is, consecutive samples at different points along the flowing stream of the contents of the mixing container 102 may agree or not. If not the contents of the mixing container may be mixed again in mixing container 102 one or more times. If they differ, the mixing container 102 may be mixed again but if a failure will be output if the specified number of times does not result in an agreement.

The reason for the redundant conductivity/temperature sensors 159c and 159s is that it provides a check on each conductivity/temperature sensors 159c and 159s. If they disagree, the mixing can be halted until the problem is worked out. The mixing container 102 may be perform another mixing of mixing container 102 and see if the measurement of the mixing container 102 is uniform.

A door lock 116 is provided adjacent the user interface door 105 to lock the user interface door. A door sensor 118 detects whether the door lock 116 is in an open or a locked position. The door sensor 118 ensures the actuators such as pinch clamps and peristaltic pump actuator fully engage the disposable circuit. The pure water flows into the disposable circuit 144 where a pair of 0.2 micron sterilizing filters 112 are located to ensure that any touch contamination making the connections for 124 are prevented from flowing into the disposable circuit 144.

A two-concentrate component system is illustrated. There are two concentrate containers—dextrose container 310 and electrolyte container 316 connectable to the rest of the fluid circuit by respective connectors 124. Note the concentrates are not limited to two—the two concentrates are shown for illustration.

In the present example in the concentrates are dextrose and electrolytes that may be used to create a ready-to-use peritoneal dialysis fluid. The dextrose concentrate may contain part of the electrolyte required to make the concentration of dextrose measurable by means of a conductivity sensor. The ratio of electrolyte to osmotic agent (e.g., dextrose) may be the lowest ratio of osmotic agent to electrolyte so that only the contents of the osmotic agent the need to be mixed if the lowest dose is required. That is, the amount of electrolyte in the dextrose container may be the amount of a predefined minimum prescribed dose of dextrose, in which case, the separate dextrose is not used. Note the number and type of the medicament concentrate may be different and within the scope of the present so the example described is not limiting of the disclosed subject matter.

Figure 1B:
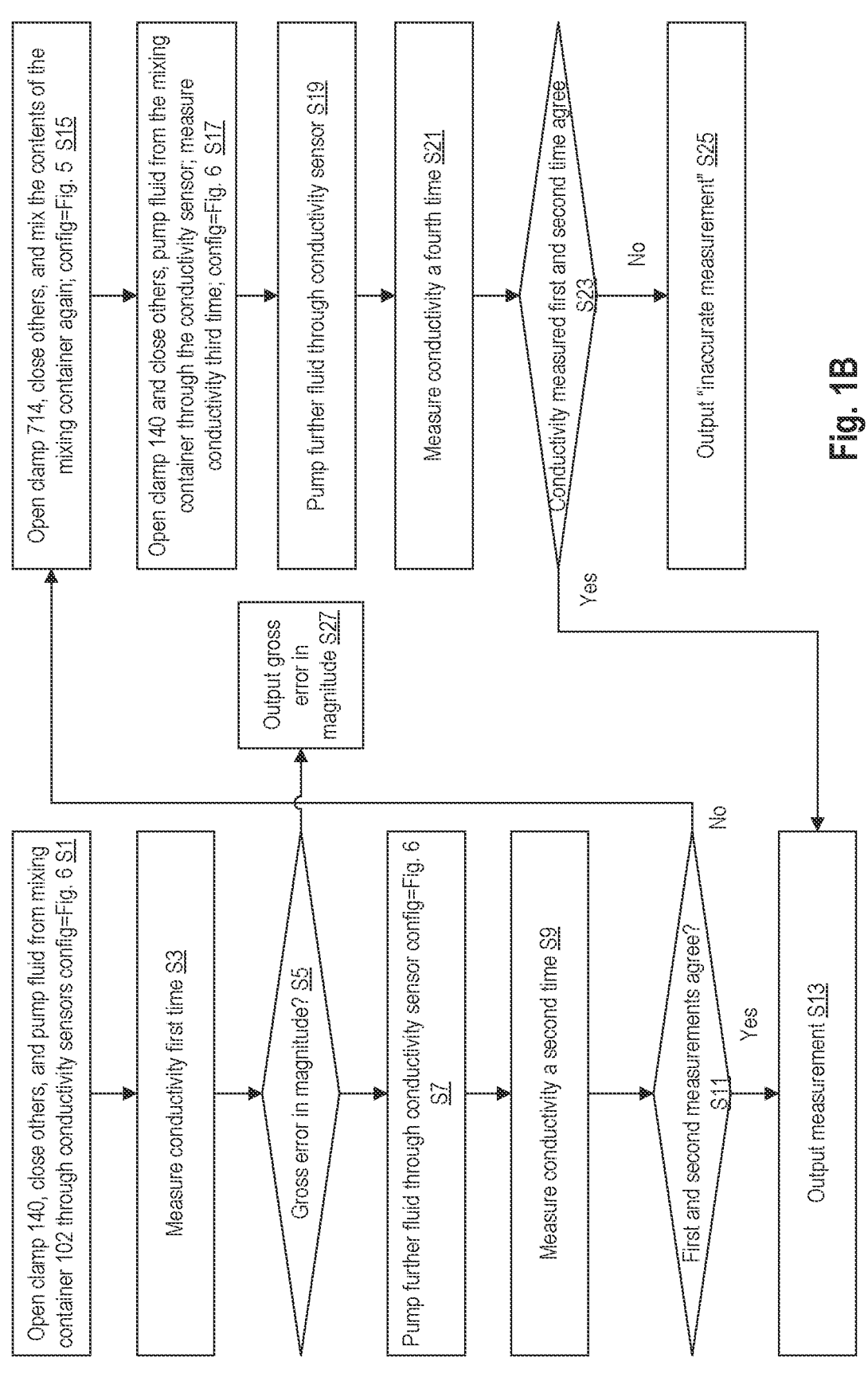
FIGS. 1B, C, and D show a flow chart of a method for preparing a ready-to-use medicament using the system of FIG. 1A according to embodiments of the disclosed subject matter.

FIG. 1B shows a procedure for reliably measuring the conductivity of a fluid. In this procedure two consecutive measurements are made. The fluid first passes through conductivity/temperature sensors 159c and 159s giving a first temperature compensated conductivity. Then the peristaltic pump 149 moves more of the fluid from the mixing container 102 and the resulting fluid is measured again. Thus, consecutive measurements cover different portions of a stream of fluid. The measurements are compared by the controller 141 and if the temperature-compensated conductivities are within a predefined range of each other then the measurement is output as a reliable measurement at S13. If the measurements show a difference in concentration beyond a predefined range, then the mixing container 102 is mixed again, and the acquisition of consecutive measurement is repeated the remix is N times and the consecutive measurements still disagree the batch may be failed. The rationale for remixing is that a difference in magnitude of the consecutive measurements is caused by inadequate mixing. Again, after mixing again and repeating the making of two consecutive measurements, the magnitudes are still outside of the predefined range of each other, then the controller outputs a measurement failure or data indicating "bad measurement." Also, after the initial measurement the controller determines if there is a predefined difference between the measurement and a predefined or calculated estimate then the algorithm will immediately output an indication and stops the process.

Note that the consecutive measurements may be done sequentially in time using one temperature-compensated conductivity measurement indicated by conductivity/temperature sensor 159c, only. The fluid then is conveyed and a temperature-compensated conductivity measurement is measured again by the same sensor. In alternative embodiments, separate pairs or single temperature-compensating may be separated along a line and the measurement generated by them may be compared instead.

Referring to FIG. 1B, at S1, the fluid whose concentration is to be measured is pumped through a conductivity/temperature sensor. The system is placed in the configuration of FIG. 6. At S3, the temperature compensated conductivity, which is proportional to the concentration, is measured a first time by flowing fluid through or past a temperature and conductivity sensors and storing a magnitude. If the disparity between an estimate and the measured compensated conductivity is beyond a threshold, then the process stops and an output indicates the type of failure (or may output a non-specific failure) S5. If there is no indication of a predefined disagreement between estimate and actual measurements, then after a time (S7) when a different volume of fluid (but part of the same stream) is in or passing the conductivity/temperature sensors, then a second measurement is made and either determined to be within a predefined range of each other or outside the range (S11). If the difference is within the range, then control proceeds to S13 and the measurement can be output to the calling routine. But if not within the range, control proceeds to S15 (the system is placed in the configuration of FIG. 5) where the contents of the mixing container are mixed again. At S17, the system is placed in the configuration of FIG. 6. A third measurement of the fluid from the mixing container is taken, the fluid moved again S19 and a fourth measurement taken S21. The controller determines if the third and fourth measurements agree at S23. If they agree (are within a defined range) then the measurement is output at S13. If not, at S25, a failure is indicated by the controller. Note that when conductivity is measure, the temperature is also measured so that a quantity representing temperature-compensated conductivity is generated. This applies to the operation of FIG. 1B and others. Another embodiment can use just a conductivity sensor rather that both a conductivity/temperature sensor if temperatures are consistently close to a predefined temperature. Note that in the specification, "bad measurement" means a measurement of the temperature-compensated conductivity could not be generated by the procedure of FIG. 1B.

Figure 1C:
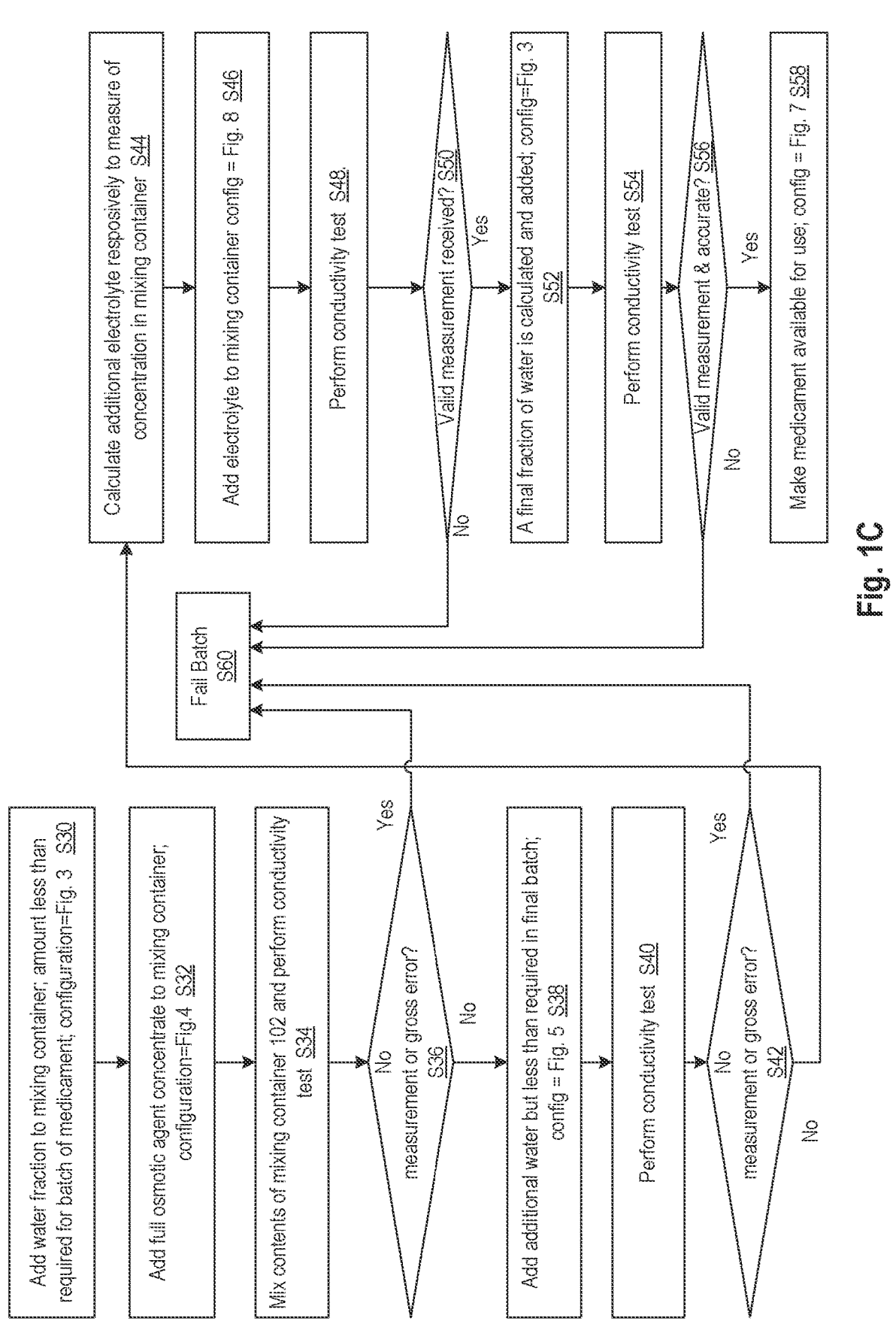
FIG. 1E shows another example system for preparing a ready to use medicament from multiple media including concentrate and water according to embodiments of the disclosed subject matter.
Figure 1D:
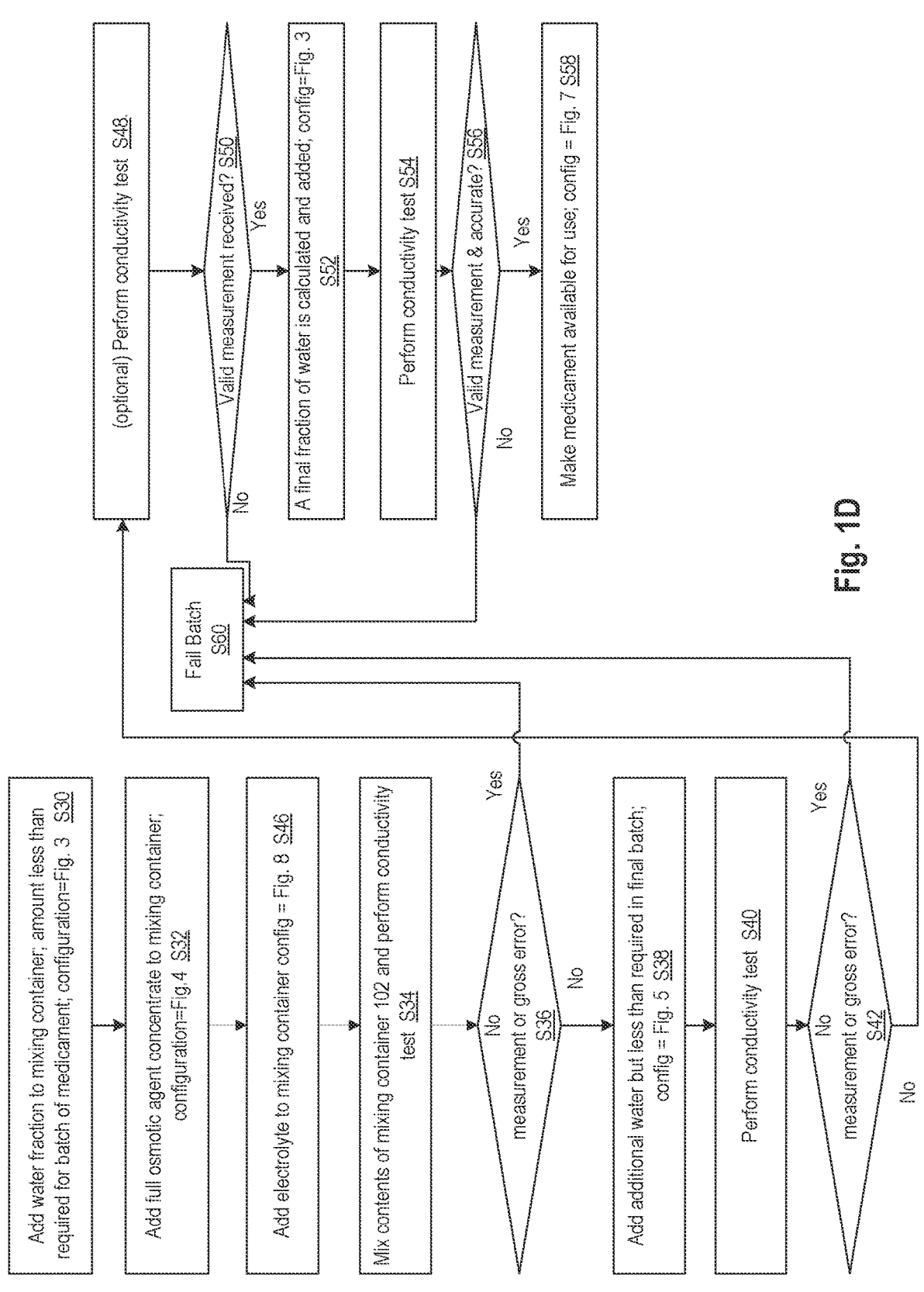
Figure 1E:
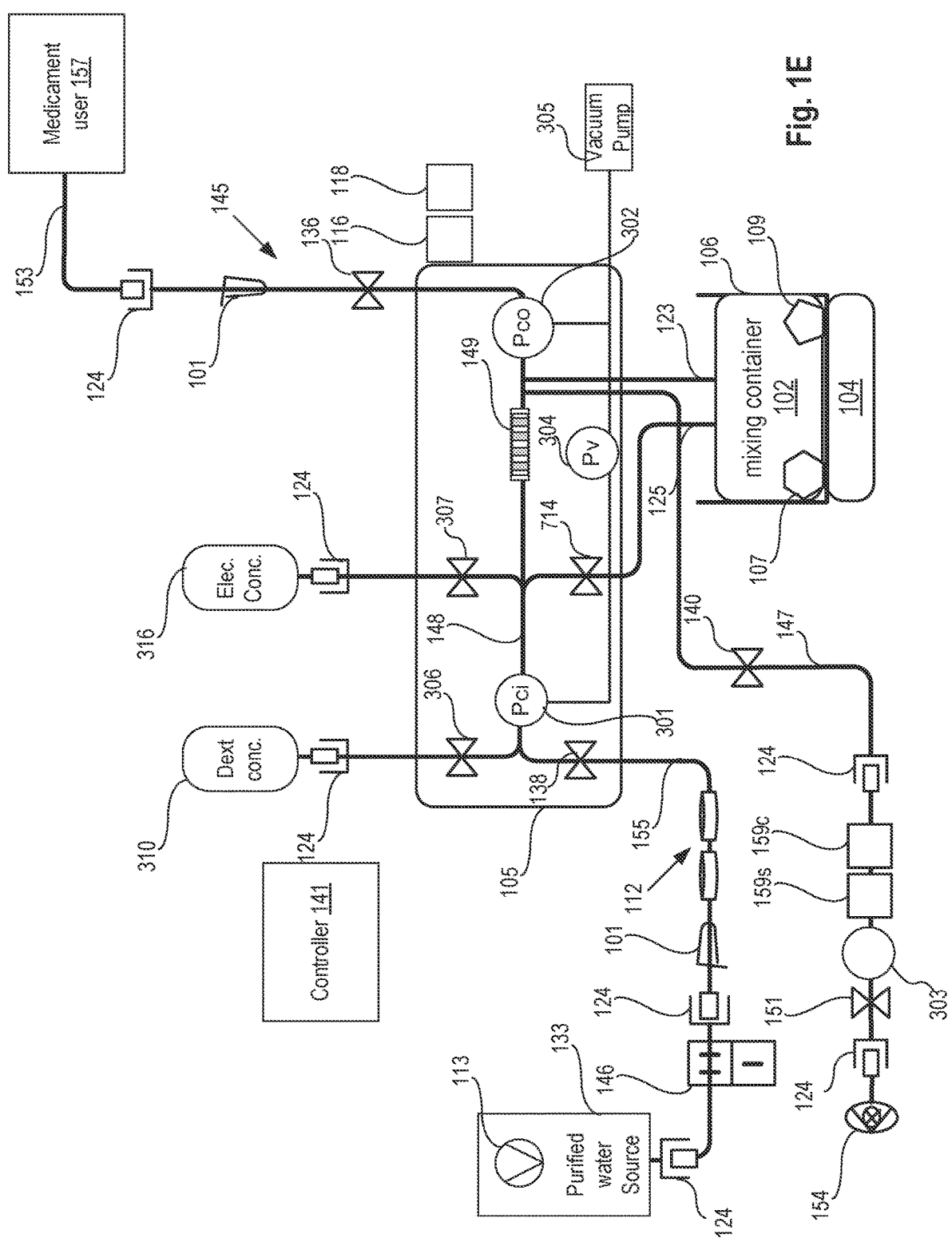

FIGS. 1C and 1D show a flow chart describing a procedure that may be executed by the controller 141 using the hardware embodiment of FIG. 1A or 1E. The procedure of FIGS. 1C-D incorporates the procedure of FIG. 1B by the description reference to a "conductivity test." When the conductivity test is referenced it means the procedure of FIG. 1B is entered and upon exiting proceeds to the next procedure element in FIGS. 1C-D.

At S30, water is added by pumping it into the mixing container 102. This is done by the controller 141 to place the system in the configuration of FIG. 3. The water pump 113 and the peristaltic pump 149 are run for a predefined number of cycles or a predefined time interval. The pumps are controlled to hold the pressure at the pressure sensor 301 at a steady pressure to provide a consistent upstream pressure for the peristaltic pump 149. The amount conveyed at S30 may be a fraction of the total estimate required for a sufficient level of dilution.

Figure 3:
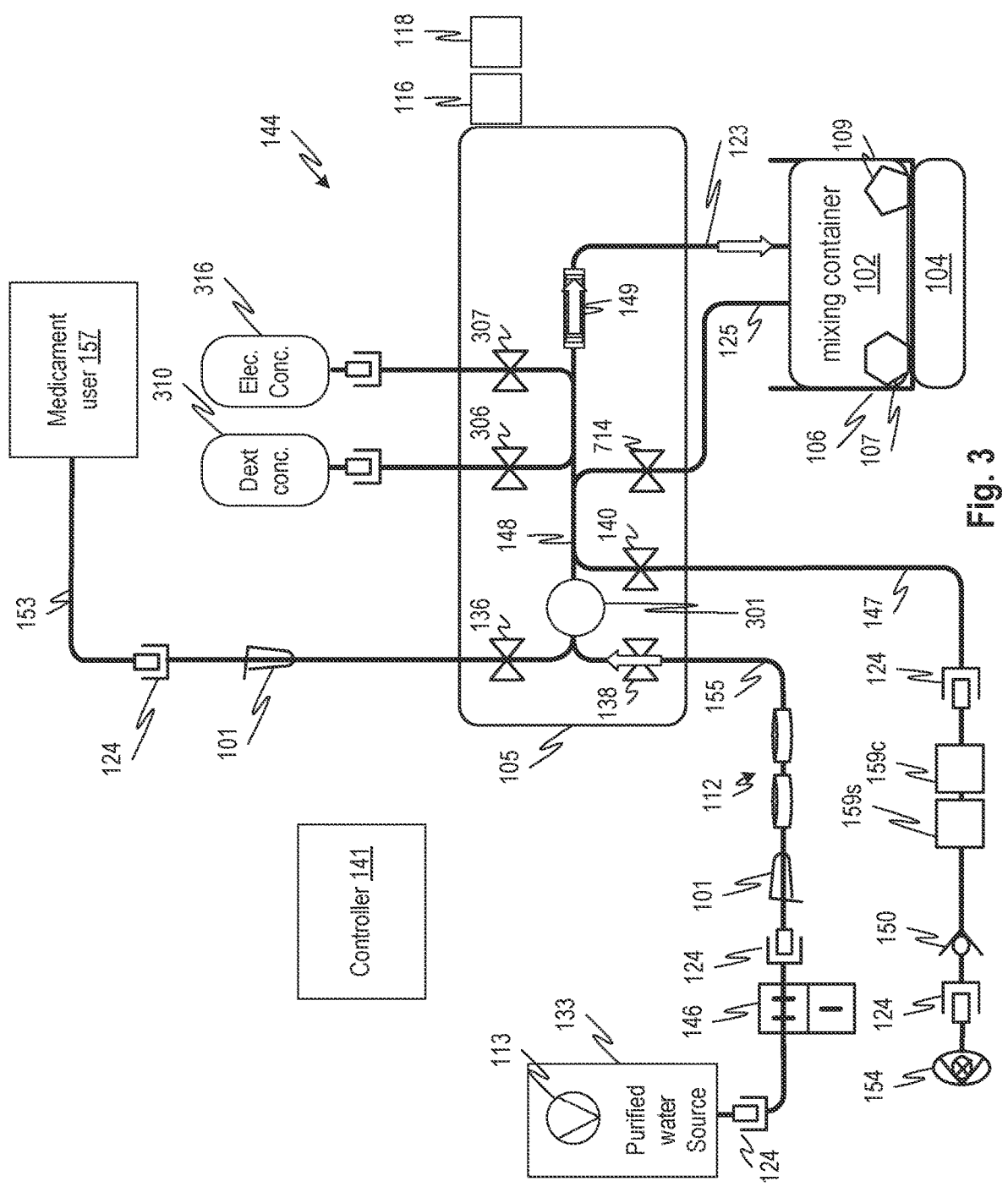
FIGS. 3 to 8 show various configurations of the system of FIG. 1A as described in the foregoing method according to embodiments of the disclosed subject matter.
Figure 4:
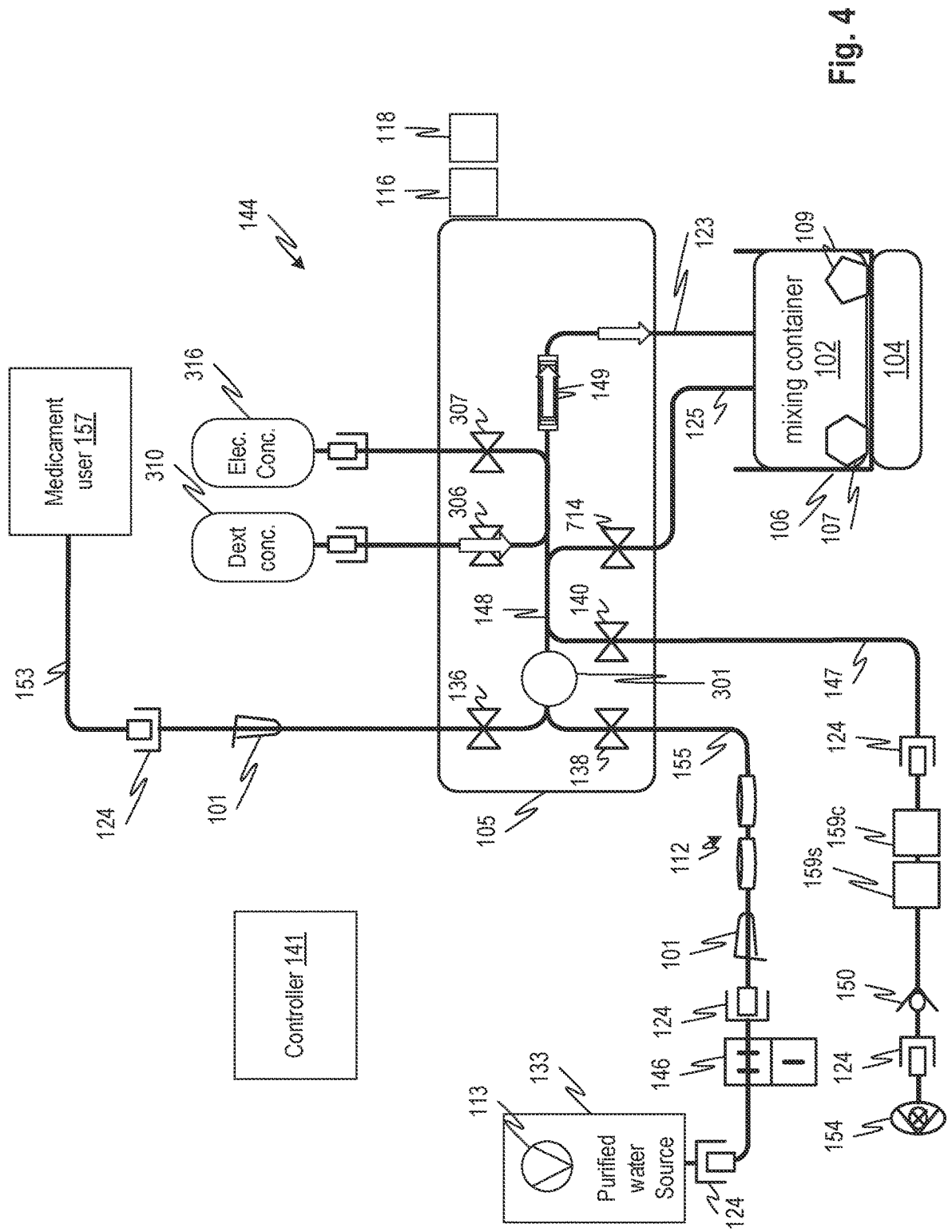

Next, at S32, all of the osmotic agent (dextrose in this example) is added to the mixing container after placing the system in the configuration of FIG. 4. In a different embodiment, the concentrate may be added until the concentrate container is empty where by a known about of the electrolyte can be stored in a memory. At S34. This works without the need for metering the concentrate by the peristaltic pump. The mass of electrolyte may be stored by the controller 141 and the conductivity test is performed. At S36 it is determined whether there was bad measurement or a gross error after the conductivity test was performed. If the signal indicates yes, then control proceeds to S60 where the batch is indicated as failed. If the determination is negative, then control proceeds to S38 where additional water is added but still insufficient to prepare a ready-to-use medicament (Configuration is that of FIG. 3). Then at S40, the conductivity test is performed again.

At S42 it is determined whether there was bad measurement or a gross error, the gross error meaning a large difference between the measurement and a predefined range representing the presumed (or possible) range magnitudes. If procedure of FIG. 1B outputs either signal, for example to indicate gross error or bad measurement, then control proceeds to S60 where the batch is indicated as failed. If the determination is negative, then control proceeds to S44 where a dose of electrolyte concentrate is conveyed to the mixing container after placing the system in the configuration of FIG. 7. At S46, electrolyte is added to the mixing container 102 after placing the system into configuration of FIG. 7. At S48, the conductivity test is performed. If a valid measurement is received at S50, then, at S52, a final fraction of the remaining water is added after placing the system in the configuration of FIG. 3. The conductivity test is performed at S54 and if a no gross error or bad measurement is indicated by the procedure of FIG. 1B (i.e., a valid measurement), then the medicament is made available for use at S58 (Configuration=FIG. 8). If the procedure of FIG. 1B indicates a gross error or bad measurement at S56, the batch is failed at S60.

The medicament may be made available for use by closing the clamps except for batch release clamp 136 and feedback controlling the peristaltic pump 149 to maintain a target pressure indicated by pressure sensor 301. The medicament user 157 may draw the fluid through the clamp 136 on-demand.

Referring now to FIG. 1D, the process of FIG. 1C is modified with respect to the order in which water, electrolyte, and osmotic agent are added. Although FIG. 1C generally describes the process of preparing the final dialysate in terms of adding water in step S30, then adding osmotic agent (e.g., dextrose) in step S32, then adding more water in step S38, then adding electrolyte in step S46, and adding yet more water in step S52, the order of these steps could be changed as shown in FIG. 1D.

In another example, the electrolyte and osmotic agent may be provided in a single concentrated mixture. Here, the concentrated mixture can be flowed into the mixing container, conductivity is measured to determine the appropriate amount of water, water is added and mixed with the concentrate. Then, another conductivity measurement may be made and a final amount of water is added and mixed. Alternatively, water may be added into the mixing container 102 first, then the electrolyte and osmotic agent concentrate, and the contents mixed. Subsequently, conductivity is measured to determine the final amount of water needed, the final amount of water is added, and mixed, to create the final medicament.

Referring now to FIG. 1E, another example system for preparing a ready to use medicament from multiple media including concentrate and water, similar to 1A, is shown. Elements having the same numbers have the same function and are not described again. The system of 1E differs from that of 1A with regard to locations of valves (136, 138, 140, 306, 307, 714) relative to the pump 149.

In FIG. 1E, disposable unit 145 has different flow paths than the disposable unit 144 of FIG. 1A, and in particular includes a pressure sensor 302 as shown in the figure. The pressure sensor 302 measure fluid pressure at the output side of the pump 149, while pressure sensor 301 measure the pressure at the input of the pump 149. Further, a valve 151 and a pressure sensor 303 are provided between connector 124 and sensor 159s on the drain conductivity line 147. Pressure sensors Pci (301) and Pco (302) are disposed on opposite sides of pump 149, and may be of a type that includes a connection to a vacuum pump 305. A pressure sensor Pv (304) may be provided on the vacuum line between sensors 301 and 302. Unless otherwise described, the operation of the system of FIG. 1E proceeds as described above with respect to FIG. 1A.

Figure 2:
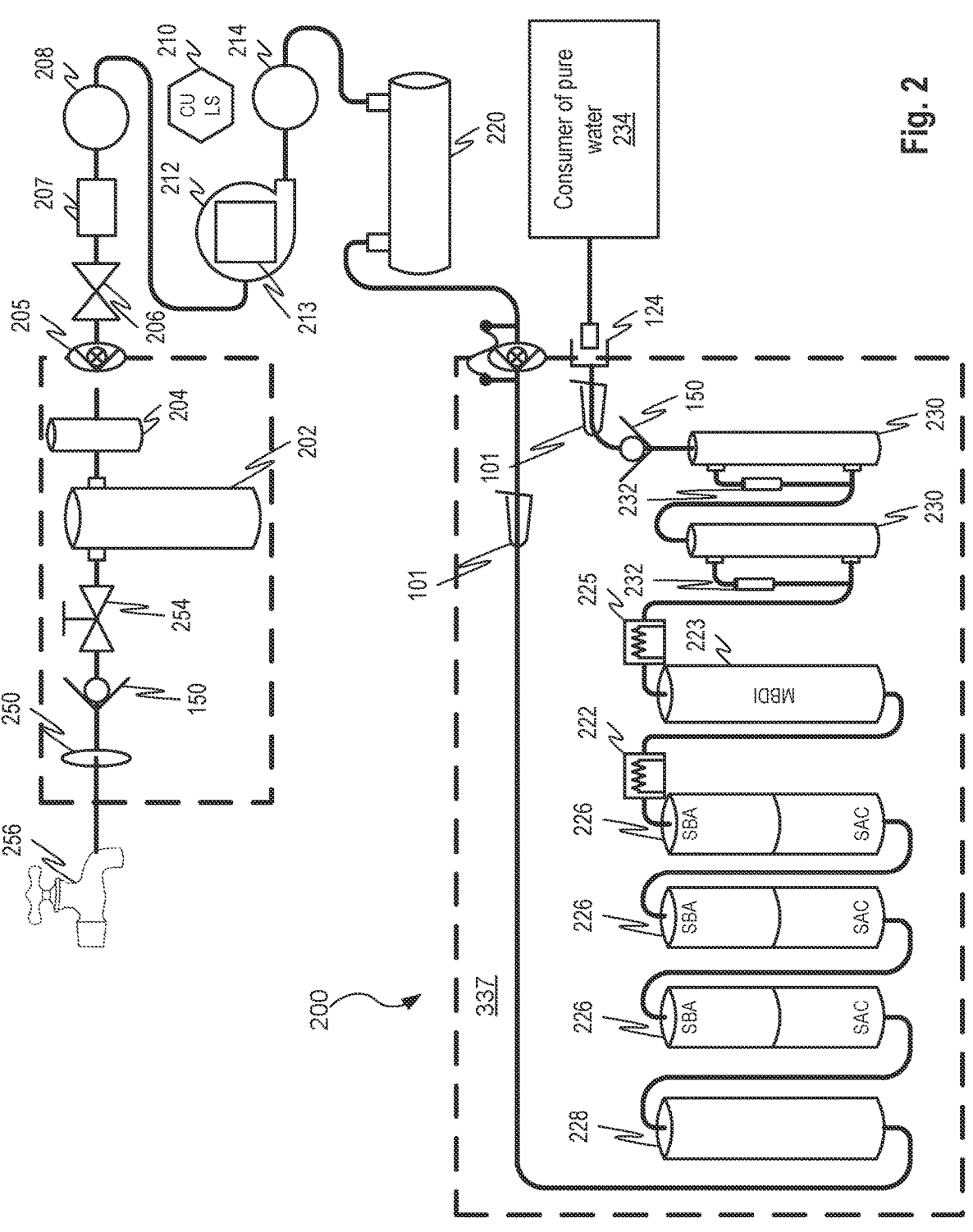
FIG. 2 shows a system for generating purified water for the system and method of FIGS. 1A through 1D according to embodiments of the disclosed subject matter.

FIG. 2 shows a water treatment plant 200 that may constitute an embodiment the purified water source 133. The water treatment plant 200 has an initial pretreatment stage that includes a connector 250 to connect to an unfiltered water source 256, for example a water tap. The water flows through a check valve 150, through a pressure regulator 254, and then through a sediment filter 202. The check valve 150 prevents backflow of the water. The water then flows through an air vent 204 that removes air from the water. The water then flows through a connector 205 that connects to a water shutoff clamp 206, a snubber 207, and a water inlet pressure sensor 208. Water is pumped by water pump 212 which has an encoder 213 for precise tracking of the water pump 212 speed. The snubber 207 reduces pressure fluctuations. The water then flows through a water output pressure sensor 214, through an ultraviolet light lamp 220 and into a filter plant 337 that performs deionization, carbon filtration, and sterilizing filtration. A combined control unit and leak sensor are indicated at 210. In the sterilizing filter plant 337, the water flows through a carbon filter 228 and three separated bed deionization filters 226 which may be resin separated bed filters. A mixed bed deionization follows the separated bed filters A resin mixed bed filter 223 is followed by first and second ultrafilters 230 and into the consumer of pure water 234. The embodiment of FIG. 1 is an example of a consumer of pure water 234.

Between a last separated bed deionization filter 226 and a mixed bed deionization filter 223 is a resistivity sensor 222 which indicates when the deionization resin separated bed filters 226 are nearing exhaustion, or at exhaustion. The deionization resin mixed bed filter 223 is still able to hold a predefined minimum magnitude of resistivity but the deionization resin separated bed filters 226 and the deionization resin mixed bed filter 223 may be replaced at the same time. In embodiments, along with the deionization resin separated bed filters 226 and the deionization resin mixed bed filter 223, the carbon filter 228 and ultrafilters 230 along with the interconnecting lines and other components may also be replaced as a single package. A current treatment can be completed in reliance on the deionization resin mixed bed filter 223 before the exhausted filters are replaced. A further resistivity sensor 225 detects unexpected problems with the deionization separated bed filter 223 upstream deionization filters which may require shutdown of the treatment and immediate replacement of the filters. Note that each of the ultrafilters 230 has an air vent 232. A check valve 150 is located downstream of the ultrafilters 230. The consumer of pure water 234 may be unit such as that of FIG. 1A which mixes a batch of medicament for use by a medicament user 157 such as a peritoneal dialysis cycler or any other type of medicament consuming device.

FIG. 3 shows the configuration for transferring water from the purified water source 133 to the mixing container 102. Note the amount of water to be transferred is a fraction, e.g., 50% of the amount of water needed to make a ready-for-use medicament. It will be observed that the clamp 138 is open and the other clamps closed and that the peristaltic pump 149 draws water. The water pump 113 and the peristaltic pump 149 operate in tandem. The speed of the water pump 113 and/or the peristaltic pump 149 may be regulated to maintain a predefined operating pressure indicated by pressure sensor 301. The pressure regulation is implemented because the peristaltic pump 149 volumetric efficiency is sensitive to its inlet pressure. In a different embodiment the peristaltic pump 149 clamp 714 is opened and the water pump 113 is used to transfer water to the mixing container 102.

FIG. 4 shows the configuration where dextrose concentrate (which may be any component of a 2-part medicament) is pumped by the peristaltic pump 149 into the mixing container 102. It will be observed by inspection of the arrows, that the clamp 306 is open and the other clamps closed. The peristaltic pump 149 is run in the right hand direction as indicated by the arrow.

Figure 5:
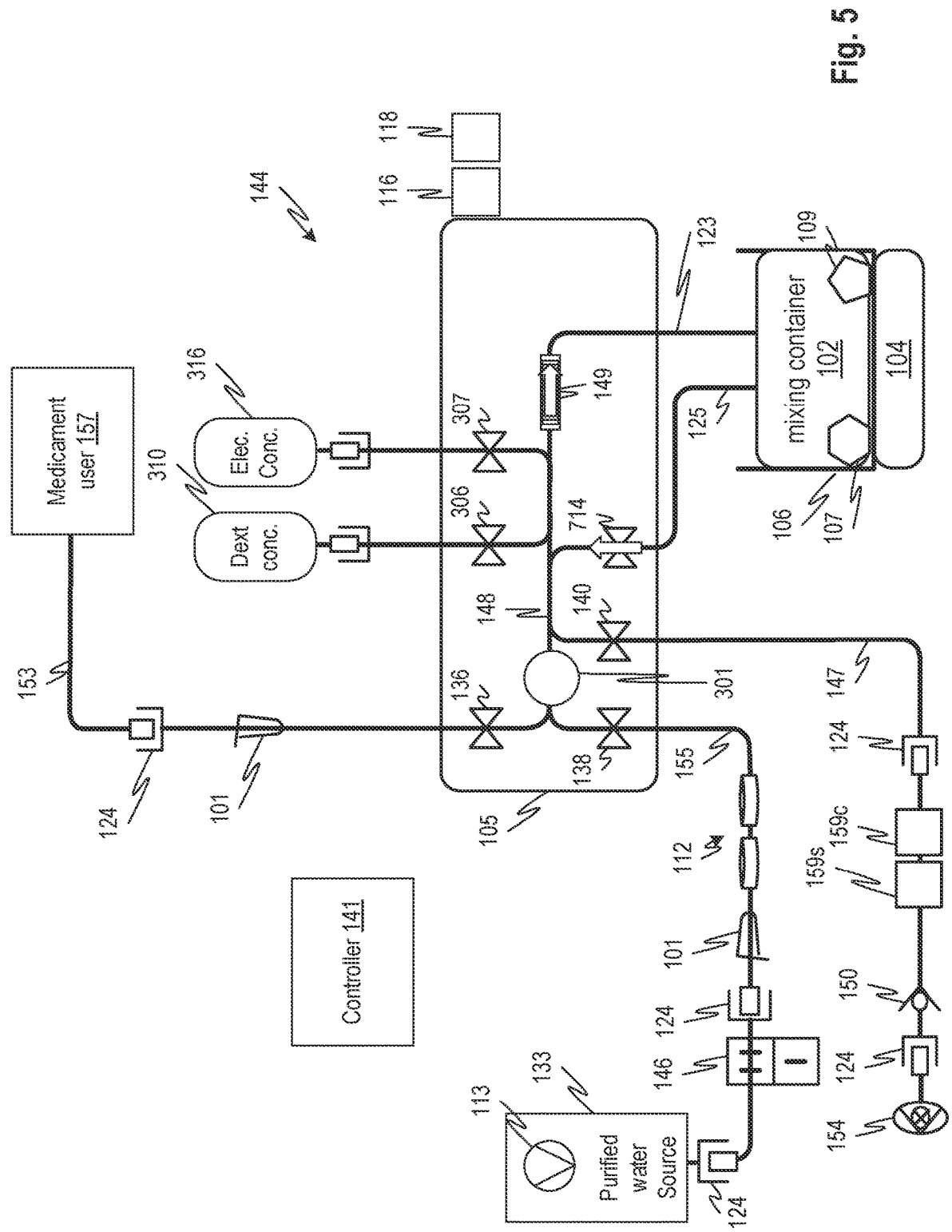

FIG. 5 shows the configuration in which the contents of the mixing container 102 are mixed by pumping fluid from the mixing container 102 back the mixing container 102 by the peristaltic pump 149 to mix its contents. All the clamps are closed except for mixing container line clamp 714. The peristaltic pump 149 is run in the right-hand direction.

Figure 6:
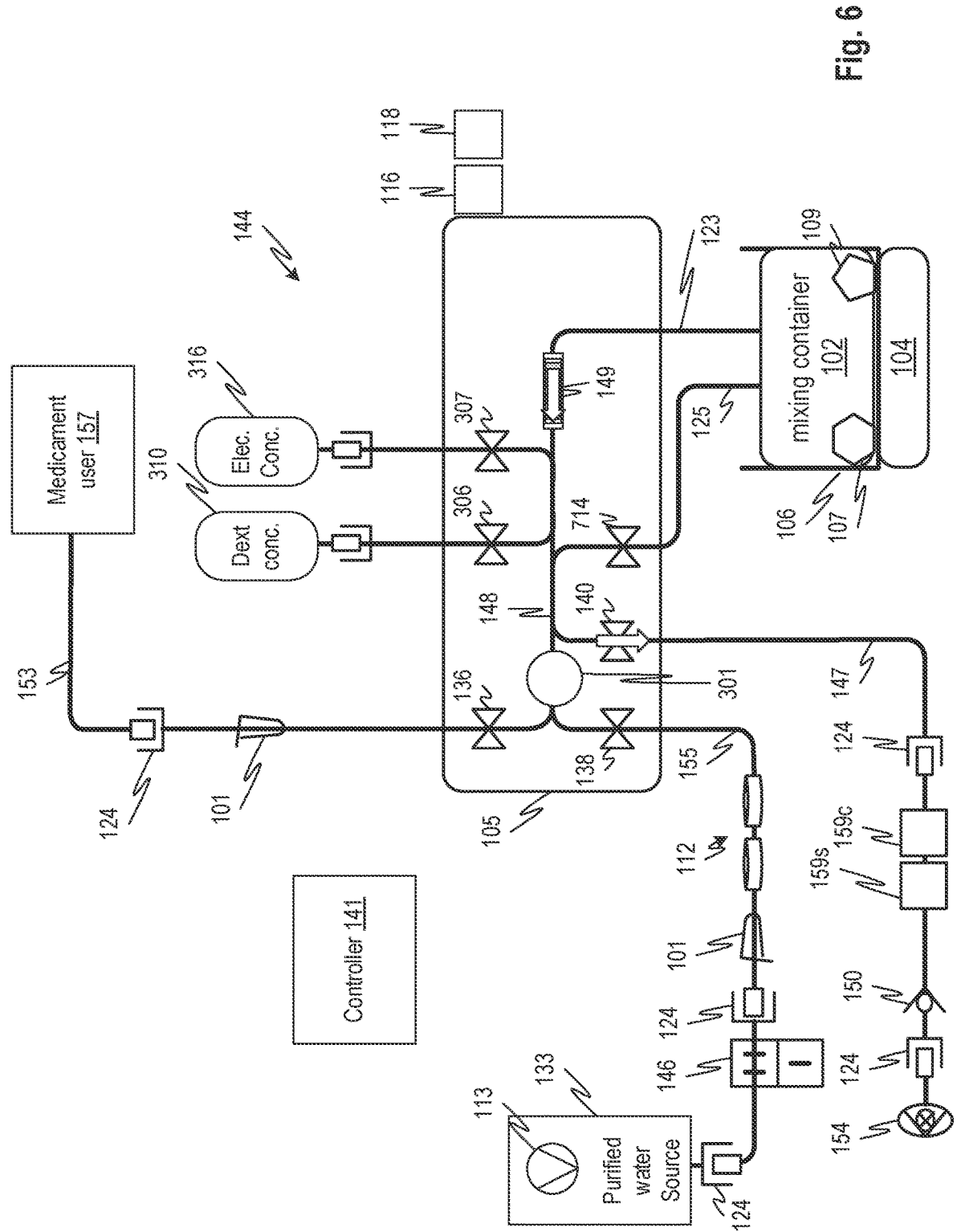

FIG. 6 shows the configuration that provides for temperature-compensating conductivity measurement. Fluid from the mixing container 102 is pumped by peristaltic pump 149 from the mixing container 102 through conductivity sensor clamp 140 through the drain conductivity line 147 and through the control conductivity/temperature sensor 159c and the safety conductivity/temperature sensor 159s. This allows a temperature-compensated conductivity to be measured. The fluid ultimately is conducted to a drain through a drain connector.

Figure 7:
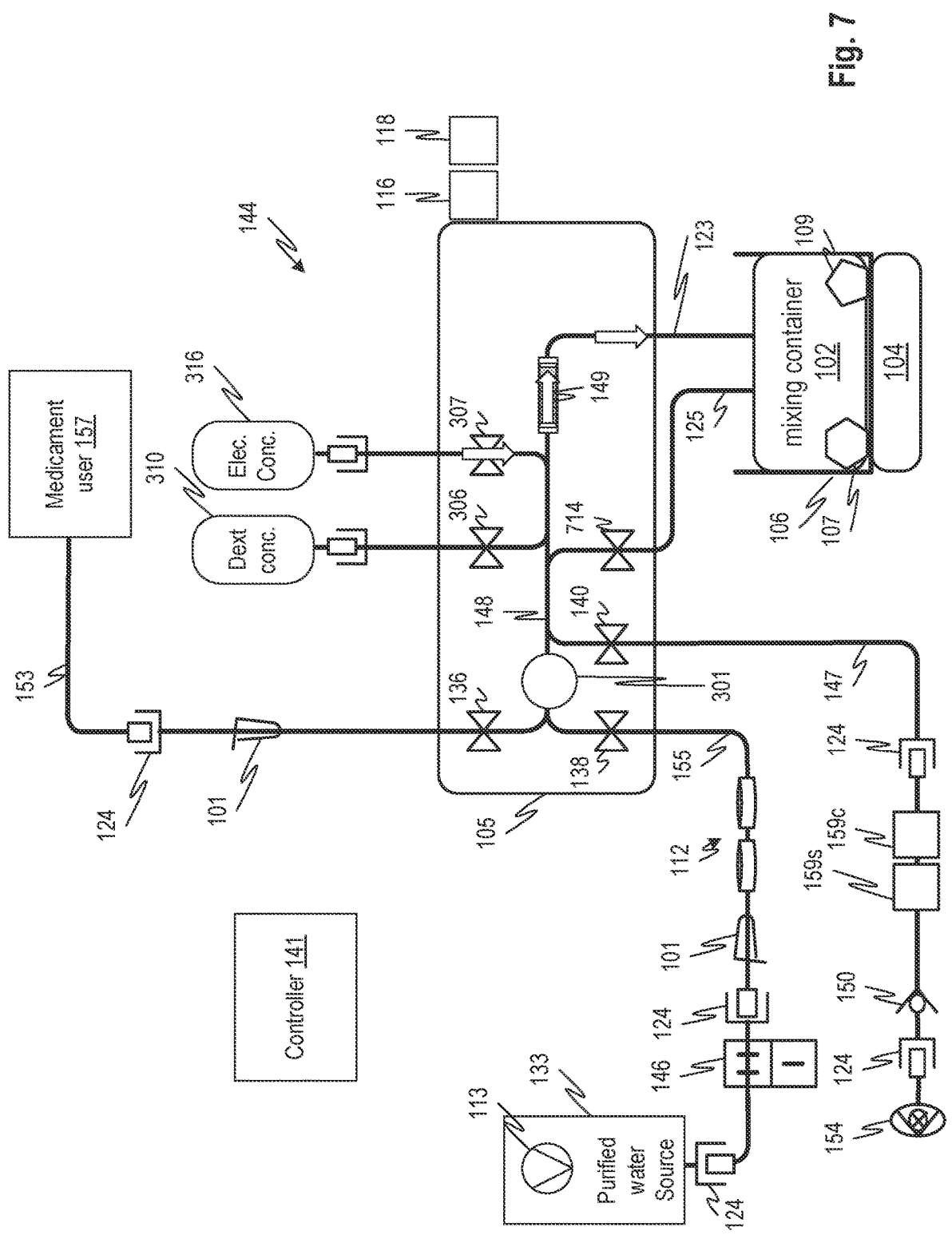

FIG. 7 shows the configuration where electrolyte is transferred through second concentrate clamp 307, pumped by peristaltic pump 149 into the mixing container 102. Note that either concentrate may be pumped first with the other concentrate being pumped second. Note also that multiple different concentrates may be provided in alternative embodiments.

Figure 8:
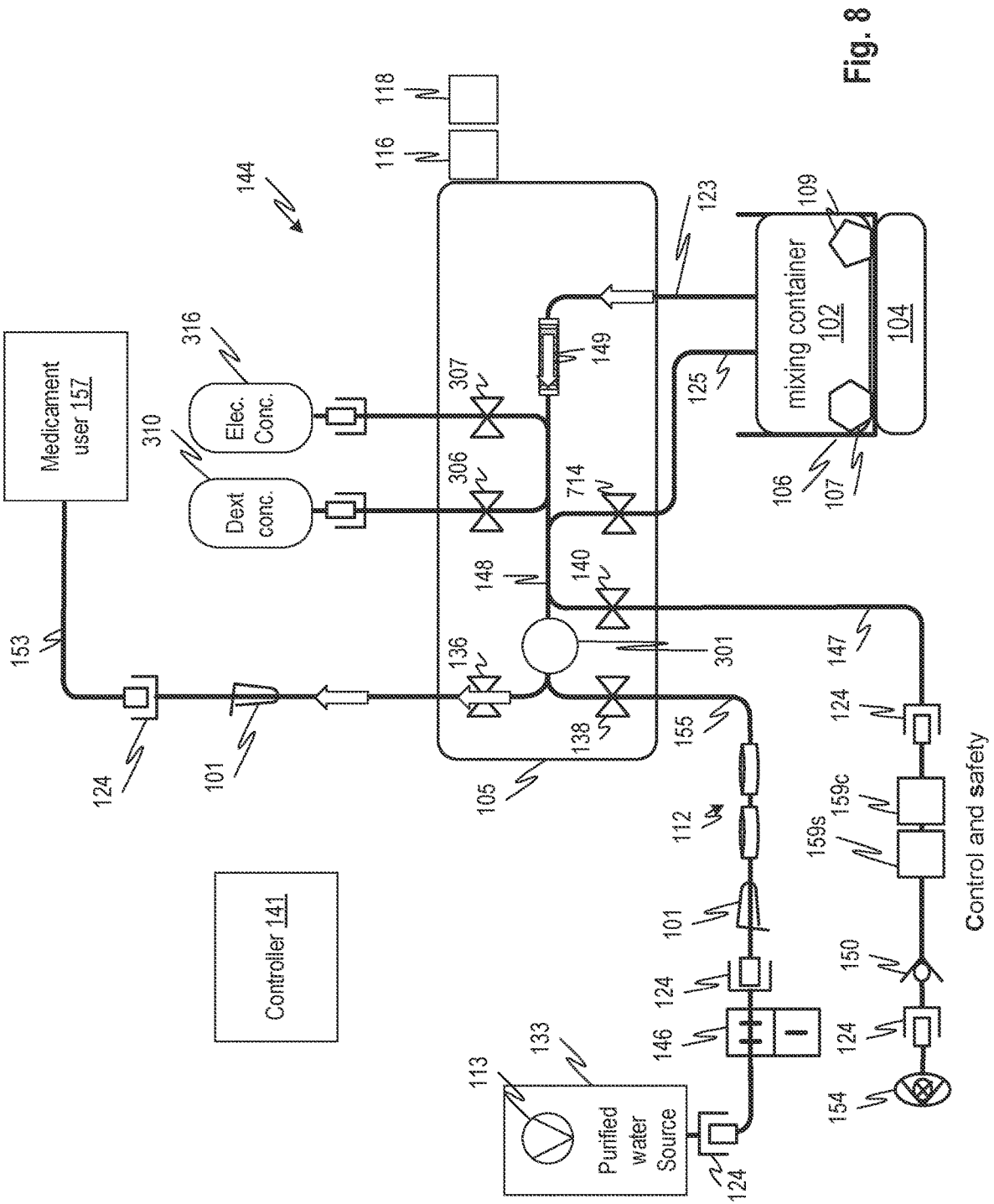

FIG. 8 shows the configuration for providing ready-to-use medicament to the medicament user 157. The ready-to-use medicament flows through the batch release clamp 136 and through the medicament line 153 pumped by the peristaltic pump 149.

However, it is also possible to utilize one or more pumps that are a part of the medicament user 157 (internal to medicament user 157) to convey the ready-to-use medicament from the mixing container 102 without the use of peristaltic pump 149. In the system of FIG. 1A, valves 136 and 714 are opened, and the medicament user 157 draws the medicament through line 153, without the use of peristaltic pump 149. For example, the medicament user 157 may be a dialysis cycler that includes a pump that is configured to draw in dialysate, such as from a bag of pre-mixed dialysate. By using this existing functionality of the cycler, the system can provide dialysate from mixing container 102 to the cycler.

Note that in alternative embodiments, there may be a single conductivity/temperature sensor instead of the pair 159c and 159s as shown. A pair of conductivity sensors may provide a check against poor accuracy or failure of one of the sensors. A method may be implemented by the controller 141 in which one of the conductivity/temperature sensors 159c or 159s may be used for the temperature-compensated conductivity signal for preparing medicament. For example, the conductivity/temperature sensor 159c. The other conductivity/temperature sensor 159s may be compared to the signal of the conductivity/temperature sensor 159c, at some point during a treatment or treatment cycle or other frequency, to determine if there is agreement between the output of the conductivity/temperature sensor 159c and conductivity/temperature sensor 159s. For example, this comparison may be done by the controller 141 at the end of the preparation of a batch to detect the reliance on erroneous output. The controller may be configured to indicate a failed batch in response to a disagreement between the two outputs. To do this, a sample of the completed batch may be conveyed through conductivity/temperature sensor 159$c$ and conductivity/temperature sensor 159$s$ to detect disagreement between the indications of outputs of the two sensors 159$s$ and 159$c$. The controller 141 may store a predefined range within which the conductivity/temperature sensor 159$c$ and conductivity/temperature sensor 159$s$ indications should be and use it to detect a low or high reading. Note that the agreement between the foregoing outputs may be checked at a variety of different frequencies and the allowed tolerance range my differ.

In alternative embodiments where the purified water source 133 has a final stage including one or more ultrafilters, the ultrafilters can be located in medicament line 153 instead of the final stage of the purified water source 133. For example, in the FIG. 2 embodiment of a purified water source 133, ultrafilters 230 can be positioned to sterile-filter the final product medicament as it is supplied to the medicament user 157. In this case, the ultrafilters 230 can be positioned in medicament line 153 instead of in the water purification plant. In other alternative embodiments, a sterilizing filter stage may be added to the medicament line 153, for example, a filter or filters such as the 0.2 micron sterilizing filters 112 or one of them. Note that in all embodiments where two or multiple sterilizing filters are provided, in further embodiments, a testable filter may alternatively to be used to form further embodiments. Testable filters are ones where the integrity of the filter membrane is tested after providing a medicament. The test may be done automatically by the controller 141, for example, by providing an air pump to perform a pressure decay test. The test may a trans-membrane pressure to test for a bubble point test. Testing may be done in a variety different ways. And the embodiments are not limited to the choice of test.

A water pump as shown at 212 in FIG. 2 or 113 in FIG. 1A, may or may not be present. This is because the peristaltic pump may pull fluid from the consumer. Also, there may be separate pumps but it may be that they are not linked in series as in the system of FIG. 1A with the FIG. 2 embodiment of a purified water source 133. Embodiments include ones where there are two separate pumps and that flow in tandem i.e., are located at points along the same flow path in a push-pull fashion. In embodiments, the water pump (212 in FIG. 2 or 133 in FIG. 1A) may be operated at a fixed rate and the peristaltic pump 149 may be controlled to mitigate variations in the pressure linking the two. This may be implemented as a negative feedback control such as a proportional, derivative, and integral (PID) control. In other embodiments the peristaltic pump 149 may be operated at a fixed rate and the water pump may be controlled. The compliance of the channel connecting the two may be adjusted by providing an accumulator or tubing of a material that adds compliance or another method to alter the compliance in a manner that makes the pressure between the pumps stable and at a predefined range of pressures.

Note that in variations of most of the embodiments, the purified water source 133 may include a container or containers of purified water such as one or more polymer bags. In such embodiments, there may be a water pump arranged in a "pull" configuration. In any of the embodiments, the medicament user 157 may include a pump. For example, the medicament user 157 may include a dialysis cycler that is configured to draw from a container of dialysis fluid.

To permit the medicament user 157 to draw medicament on-demand, the controller may be programmed to maintain a constant pressure that is compatible with a pump in the medicament user 157. For example, the pressure-based control using the pressure sensor 301 may maintain a pressure that mimics a simple container that allows the medicament user 157 to draw from a container of dialysis fluid.

In embodiments, the medicament user 157 can use its own pump to move fluid from the mixing container 102 without the use of pump 149. In this example, valves 136 and 714 will be opened, and the medicament user 157 will operate its pump to draw fluid form the mixing container 102.

An alternative to metering with the pump 149 is to allow the concentrates to empty entirely into the mixing container 102 by gravity. The mass or volume of the concentrates in each of the concentrate containers may be stored by the controller allowing the controller to calculate the amount of water required to complete a batch of water to provide a ready-use medicament.

According to embodiments, the disclosed subject matter includes an admixing device, comprising. A mixing machine has a controller. The mixing machine is configured to engage with a fluid circuit, the fluid circuit has a connector configured for connection to a source of pure water and a connector configured for connecting respectively to at least one source of medicament concentrate. The fluid circuit has a mixing container. The mixing machine further has a pressure sensor configured to engage with the fluid circuit to indicate a pressure of a medicament manifold line of the fluid circuit with a connector configured to connect to a selected one of several different medicament user devices. The controller is configured to, by feedback control, maintain a respective pressure applied to said machine controller pump actuator being applied at an inlet to said selected one of several different medicament user devices or storage containers. The selected one of said plurality of pressures corresponding respectively to a selected one of multiple different medicament user devices.

In a variation of the embodiments, the medicament user device includes a peritoneal dialysis cycler.

In a variation of the embodiments, the controller is configured to actively control said predefined pressure using feedback control. In a variation of the embodiments, the mixing machine has a pump actuator and said fluid circuit has a pumping portion configured to engage said pump actuator. In variations of embodiment the embodiments the flow switch the pump actuator is a peristaltic pump actuator.

In a variation thereof, the disclosed embodiments includes ones in which the mixing machine and the pumping portion are connected between said mixing container and said manifold line.

In a variation thereof, the disclosed embodiments includes ones in which said pump actuator runs in a first direction to transfer medicament and to said manifold to the medicament user, and an opposite direction to proportion concentrate and water in said mixing container.

In a variation thereof, the disclosed embodiments includes ones in which said manifold and said pressure sensor are directly connected to said pumping portion.

In a variation thereof, the disclosed embodiments includes ones in which the pump actuator is configured to pump fluid into and out of said mixing container to mix the contents of said mixing container.

In a variation thereof, the disclosed embodiments includes ones in which said manifold line is connected to valve portions of said fluid circuit and said mixing machine having valve actuators that engage with the valve portions, the fluid circuit having a valve portion engageable with a respective valve actuator for each of said medicament concentrates, one for said medicament user device, one for said one for said source of pure water, one for a drain, and one for said mixing container, wherein a line with said pumping portion that connects the manifold line to said mixing container has no valve portion.

In a variation thereof, the disclosed embodiments includes ones in which said mixing container has two lines, both of which connect the mixing container with the manifold line, one connecting to the manifold line through the pumping portion.

In a variation thereof, the disclosed embodiments includes ones in which said manifold line is connectable to a drain.

In a variation thereof, the disclosed embodiments includes ones in which said pressure sensor is positioned to detect pressure in said manifold line.

According to embodiments, the disclosed subject matter includes a proportioning device. A proportioning machine has a temperature-compensating conductivity sensor, a controller, and pump actuator. A fluid circuit is engageable with said pump actuator The fluid circuit has connections for a source of water and one or more medicament concentrates. The fluid circuit having a mixing container. The controller is configured to mix contents of said mixing container at a first time. The proportioning machine controller pump actuator being controlled to sample fluid from said mixing container, to pass the samples from the mixing container through said temperature-compensating conductivity sensor, and to compare conductivities of said samples, wherein the samples are taken at different points in time as the fluid flows from said mixing container.

Said controller is configured to mix contents of said mixing container a second time if said conductivities differ by a predefined magnitude.

In variations thereof, the disclosed embodiments includes ones in which the mixing container has two lines and said controller mixes contents of said mixing container by flowing fluid into one of said two lines and out of said mixing container by flowing fluid out of another of said two lines. In variations thereof, the disclosed embodiments includes ones in which said pump runs in a single same direction when it pumps medicament concentrate and water into said mixing container.

According to embodiments the disclosed subject matter includes proportioning device.

A proportioning machine has a controller and a pump actuator. A fluid circuit engageable with said pump actuator. The fluid circuit has a manifold connected to a fluid source and one or more concentrate sources, an outlet for a drain, and an outlet for diluted concentrate connectable to a predefined cycler.

The fluid circuit has a mixing container connected to the pump and the manifold at two locations of the mixing container. The controller is configured to cause the pump to pump fluid into the mixing container while running in a same direction and to pump fluid from said mixing container in an opposite direction into said manifold and out of said mixing container. The proportioning machine is configured to pressurize said manifold to predefined pressure for a selected one of a plurality of cyclers, each cycler being different in terms of the inlet pressure range to allow drawing of medicament from the pressurized manifold a pressure that is compatible with the selected one of the plurality of cyclers.

In variations thereof, the disclosed embodiments includes ones in which said pump runs only in a first direction when it proportions medicament concentrate and water in said mixing container.

In variations thereof, the disclosed embodiments includes ones in which the mixing container has two lines connected respectively to an inlet of said mixing container and to an outlet of said mixing container where said inlet and outlet are connect respectively to an inlet and an outlet of said pump.

According to embodiments the disclosed subject matter includes a proportioning device. A proportioning machine with a controller and a pump actuator. A fluid circuit is engageable with said pump actuator. The fluid circuit has a manifold connected to a fluid source and one or more concentrate sources, an outlet for a drain, and an outlet for diluted concentrate connectable to a predefined cycler.

According to embodiments the disclosed subject matter includes the fluid circuit has a mixing container connected to the pump and the manifold at two locations of the mixing container.

The controller is configured to cause the pump to pump fluid into the mixing container while running in a same direction and to pump fluid from said mixing container in an opposite direction into said manifold and out of said mixing container.

The proportioning machine is configured to pressurize said manifold to a predefined pressure required by a selected one of a plurality of cyclers.

The manifold has N lines stemming from the manifold, each of said N lines, except one, having a respective valve portion such that there are N−1 valve portions.

According to embodiments the disclosed subject matter includes a proportioning device. An admixing machine with a controller, actuators configured to engage with predefined portions of a fluid circuit. The controller is configured to mix fluid in said fluid circuit. The controller is configured to control one or a plurality of the actuators to convey mixed fluid from the fluid circuit to a drain connected thereto, the drain having at least one conductivity sensor. the controller is further configured to control the plurality of the actuators to determine conductivities of the fluid in the drain at least two times as the fluid is conveyed through the fluid circuit to the drain such that the conductivities corresponding to the two different times are measured.

The controller is further configured to, if the conductivities determined at said at least two times of the fluid sampled are within a predefined difference of each other, make the contents of the mixing container available for use and if they are not, to mix the fluid in the fluid circuit again.

According to embodiments the disclosed subject matter includes herein said at least two times are two times. According to embodiments the disclosed subject matter includes, if the if the conductivities determined at said at least two times of the fluid sampled are within the predefined difference, to pump fluid to a fluid consuming device or permit the fluid consumer to pump it from the fluid circuit.

According to embodiments the disclosed subject matter includes the fluid consuming device includes a dialysis cycler.

According to embodiments the disclosed subject matter includes said controller is configured to, if either of said conductivities is outside of a predefined range, then to control the plurality of actuators to prevent the use of the of mixed fluid mixed thereby.

According to embodiments, the disclosed subject matter includes a proportioning method. The method includes using a controller of an admixing machine, mixing a fluid in a fluid circuit. The method includes using the controller, mixing a fluid.

using the controller, controlling one or a plurality of actuators to convey a mixed fluid resulting from said mixing to a drain having fluid conductivity sensors.

The controller is configured to control one or a plurality of the actuators to convey mixed fluid from the fluid circuit to a drain connected thereto, the drain having at least one conductivity sensor.

The controller is further configured to control the plurality of the actuators to determine conductivities of the fluid in the drain at least two times as the fluid is conveyed through the fluid circuit to the drain such that the conductivities corresponding to the two different times are measured. The controller is further configured to, if the conductivities determined at said at least two times of the fluid sampled are within a predefined difference of each other and if they are not, to mix the fluid in the fluid circuit again.

The method includes are such that said at least two times are two times.

In variations thereof, the method includes, if the if the conductivities determined at said at least two times of the fluid sampled are within the predefined difference, to pump fluid to a fluid consuming method or permit the fluid consumer to pump it from the fluid circuit.

The method may include the fluid consuming method includes a dialysis cycler.

In variations thereof, the flow switch, if either of said conductivities is outside of a predefined range, then to control the plurality of actuators to prevent the use of the of a mixed fluid mixed thereby.

According to embodiments, the disclosed subject matter includes a system for preparing medicament. An admixing machine with flow actuators, one or more pump actuators, at least one pressure sensor, and a controller. The controller is connected to said pump and flow actuators to control the pump and the flow actuators to generate and control flows in a fluid circuit that has a mixing container and a manifold. The manifold is connected by two lines to the mixing container, one line controlled by a clamp and the other controlled by the pump.

In a variation of the embodiments, the flow switch the manifold connects a medicament user or storage container. In a variation of the embodiments, the flow switch and manifold connects to a source of pure water. In variations thereof, the disclosed subject includes ones in which the flow switch the manifold connects one or more concentrates.

In variations thereof, the disclosed subject includes ones in which the manifold connects a drain line with conductivity sensors.

In variations thereof, the disclosed subject includes ones in which the controller is configured to control the pump and flow actuators to mix at least one concentrate and water in said mixing container such that a ready-to-use medicament is generated in said mixing container.

In variations thereof, the disclosed subject includes ones in which the controller is further configured to control said flow and pump actuators responsively to a pressure sensor and selection data received by the controller, the selection data indicating a target pressure in a fluid channel that connects the admixing machine to a selected medicament-consuming device.

In variations thereof, the disclosed subject includes ones in which the selected medicament-consuming device includes a dialysis cycler.

In variations thereof, the disclosed subject includes ones in which the selected medicament-consuming device includes a peritoneal dialysis cycler.

In variations thereof, the disclosed subject includes ones in which controller is configured to run the pump in the first direction to convey medicament from the mixing container to draw one or more concentrates the pump that can run in first and second directions responsively to a first direction, wherein the controller is configured to cause said pump to run in the first direction when pumping said one or more concentrates and water and in second direction opposite direction pumping through a flow through the peristaltic pump.

In variations thereof, the disclosed subject includes ones in which the manifold has no barriers and constitutes a single volume across its entirety.

According to embodiments, the disclosed subject matter includes n admixing device, comprising. A mixing machine has a controller. The mixing machine is configured to engage with a fluid circuit, the fluid circuit has a connector configured for connection to a source of pure water and a connector configured for connecting respectively to at least one source of medicament concentrate. The fluid circuit has a mixing container. The mixing machine further has a pressure sensor configured to engage with the fluid circuit to indicate a pressure of a medicament manifold line of the fluid circuit with a connector configured to connect to a selected one of several different medicament user devices. The controller is configured to, by feedback control, maintain a respective pressure applied to said machine controller pump actuator being applied at an inlet to said selected one of several different medicament user devices or storage containers. The selected one of said plurality of pressures corresponding respectively to a selected one of multiple different medicament user devices.

In a variation of the embodiments, the medicament user device includes a peritoneal dialysis cycler.

In a variation of embodiment, the controller is configured to actively control said predefined pressure using feedback control. In a variation of the embodiments, the mixing machine has a pump actuator and said fluid circuit has a pumping portion configured to engage said pump actuator. In variations of embodiment the embodiments the flow switch the pump actuator is a peristaltic pump actuator.

In a variation thereof, the disclosed embodiments includes ones in which the mixing machine and the pumping portion are connected between said mixing container and said manifold line.

In a variation thereof, the disclosed embodiments includes ones in which said pump actuator runs in a first direction to transfer medicament and to said manifold to the medicament user, and an opposite direction to proportion concentrate and water in said mixing container.

In a variation thereof, the disclosed embodiments includes ones in which said manifold and said pressure sensor are directly connected to said pumping portion.

In a variation thereof, the disclosed embodiments includes ones in which the pump actuator is configured to pump fluid into and out of said mixing container to mix the contents of said mixing container.

In a variation thereof, the disclosed embodiments includes ones in which said manifold line is connected to valve portions of said fluid circuit and said mixing machine having valve actuators that engage with the valve portions, the fluid circuit having a valve portion engageable with a respective valve actuator for each of said medicament concentrates, one for said medicament user device, one for said one for said source of pure water, one for a drain, and one for said mixing container, wherein a line with said pumping portion that connects the manifold line to said mixing container has no valve portion.

In a variation thereof, the disclosed embodiments includes ones in which said mixing container has two lines, both of which connect the mixing container with the manifold line, one connecting to the manifold line through the pumping portion.

In a variation thereof, the disclosed embodiments includes ones in which said manifold line is connectable to a drain.

In a variation thereof, the disclosed embodiments includes ones in which said pressure sensor is positioned to detect pressure in said manifold line.

According to embodiments, the disclosed subject matter includes a proportioning device. A proportioning machine has a temperature-compensating conductivity sensor, a controller, and pump actuator. A fluid circuit is engageable with said pump actuator The fluid circuit has connections for a source of water and one or more medicament concentrates. The fluid circuit having a mixing container. The controller is configured to mix contents of said mixing container at a first time. The proportioning machine controller pump actuator being controlled to sample fluid from said mixing container, to pass the samples from the mixing container through said temperature-compensating conductivity sensor, and to compare conductivities of said samples, wherein the samples are taken at different points in time as the fluid flows from said mixing container.

Said controller is configured to mix contents of said mixing container a second time if said conductivities differ by a predefined magnitude.

In variations thereof, the disclosed embodiments includes ones in which the mixing container has two lines and said controller mixes contents of said mixing container by flowing fluid into one of said two lines and out of said mixing container by flowing fluid out of another of said two lines. In variations thereof, the disclosed embodiments includes ones in which said pump runs in a single same direction when it pumps medicament concentrate and water into said mixing container.

According to embodiments the disclosed subject matter includes proportioning device. A proportioning machine has a controller and a pump actuator. A fluid circuit engageable with said pump actuator. The fluid circuit has a manifold connected to a fluid source and one or more concentrate sources, an outlet for a drain, and an outlet for diluted concentrate connectable to a predefined cycler.

The fluid circuit has a mixing container connected to the pump and the manifold at two locations of the mixing container. The controller is configured to cause the pump to pump fluid into the mixing container while running in a same direction and to pump fluid from said mixing container in an opposite direction into said manifold and out of said mixing container. The proportioning machine is configured to pressurize said manifold to predefined pressure for a selected one of a plurality of cyclers, each cycler being different in terms of the inlet pressure range to allow drawing of medicament from the pressurized manifold a pressure that is compatible with the selected one of the plurality of cyclers.

In variations thereof, the disclosed embodiments includes ones in which said pump runs only in a first direction when it proportions medicament concentrate and water in said mixing container.

In variations thereof, the disclosed embodiments includes ones in which the mixing container has two lines connected respectively to an inlet of said mixing container and to an outlet of said mixing container where said inlet and outlet are connect respectively to an inlet and an outlet of said pump.

According to embodiments the disclosed subject matter includes a proportioning device. A proportioning machine with a controller and a pump actuator. A fluid circuit is engageable with said pump actuator. The fluid circuit has a manifold connected to a fluid source and one or more concentrate sources, an outlet for a drain, and an outlet for diluted concentrate connectable to a predefined cycler.

According to embodiments the disclosed subject matter includes the fluid circuit has a mixing container connected to the pump and the manifold at two locations of the mixing container.

The controller is configured to cause the pump to pump fluid into the mixing container while running in a same direction and to pump fluid from said mixing container in an opposite direction into said manifold and out of said mixing container.

The proportioning machine is configured to pressurize said manifold to a predefined pressure required by a selected one of a plurality of cyclers.

The manifold has N lines stemming from the manifold, each of said N lines, except one, having a respective valve portion such that there are N−1 valve portions.

According to embodiments the disclosed subject matter includes a proportioning device. An admixing machine with a controller, actuators configured to engage with predefined portions of a fluid circuit. The controller is configured to mix fluid in said fluid circuit. The controller is configured to control one or a plurality of the actuators to convey mixed fluid from the fluid circuit to a drain connected thereto, the drain having at least one conductivity sensor. the controller is further configured to control the plurality of the actuators to determine conductivities of the fluid in the drain at least two times as the fluid is conveyed through the fluid circuit to the drain such that the conductivities corresponding to the two different times are measured.

The controller is further configured to mix the fluid in the fluid circuit again if the conductivities determined at said at least two times of the fluid sampled are within a predefined difference of each other and if they are not.

According to embodiments the disclosed subject matter includes herein said at least two times are two times. According to embodiments the disclosed subject matter includes, if the if the conductivities determined at said at least two times of the fluid sampled are within the predefined difference, to pump fluid to a fluid consuming device or permit the fluid consumer to pump it from the fluid circuit.

According to embodiments the disclosed subject matter includes the fluid consuming device includes a dialysis cycler.

According to embodiments the disclosed subject matter includes said controller is configured to, if either of said conductivities is outside of a predefined range, then to control the plurality of actuators to prevent the use of the of mixed fluid mixed thereby.

According to embodiments, the disclosed subject matter includes a proportioning method. The method includes using a controller of an admixing machine, mixing a fluid in a fluid circuit. The method includes using the controller, mixing a fluid.

using the controller, controlling one or a plurality of actuators to convey a mixed fluid resulting from said mixing to a drain having fluid conductivity sensors.

The controller is configured to control one or a plurality of the actuators to convey mixed fluid from the fluid circuit to a drain connected thereto, the drain having at least one conductivity sensor.

The controller is further configured to control the plurality of the actuators to determine conductivities of the fluid in the drain at least two times as the fluid is conveyed through the fluid circuit to the drain such that the conductivities corresponding to the two different times are measured. The controller is further configured to, if the conductivities determined at said at least two times of the fluid sampled are within a predefined difference of each other and if they are not, to mix the fluid in the fluid circuit again.

The method includes are such that said at least two times are two times.

In variations thereof, the method includes, if the if the conductivities determined at said at least two times of the fluid sampled are within the predefined difference, to pump fluid to a fluid consuming method or permit the fluid consumer to pump it from the fluid circuit.

The method may include the fluid consuming method includes a dialysis cycler.

In variations thereof, the flow switch, if either of said conductivities is outside of a predefined range, then to control the plurality of actuators to prevent the use of the of a mixed fluid mixed thereby.

According to embodiments, the disclosed subject matter includes a system for preparing medicament. An admixing machine with flow actuators, one or more pump actuators, at least one pressure sensor, and a controller. The controller is connected to said pump and flow actuators to control the pump and the flow actuators to generate and control flows in a fluid circuit that has a mixing container and a manifold. The manifold is connected by two lines to the mixing container, one line controlled by a clamp and the other controlled by the pump.

In a variation of the embodiments, the flow switch the manifold connects a medicament user or storage container. In a variation of the embodiments, the flow switch and manifold connects to a source of pure water. In variations thereof, the disclosed subject includes ones in which the flow switch the manifold connects one or more concentrates.

In variations thereof, the disclosed subject includes ones in which the manifold connects a drain line with conductivity sensors.

In variations thereof, the disclosed subject includes ones in which the controller is configured to control the pump and flow actuators to mix at least one concentrate and water in said mixing container such that a ready-to-use medicament is generated in said mixing container.

In variations thereof, the disclosed subject includes ones in which the controller is further configured to control said flow and pump actuators responsively to a pressure sensor and selection data received by the controller, the selection data indicating a target pressure in a fluid channel that connects the admixing machine to a selected medicament-consuming device.

In variations thereof, the disclosed subject includes ones in which the selected medicament-consuming device includes a dialysis cycler.

In variations thereof, the disclosed subject includes ones in which the selected medicament-consuming device includes a peritoneal dialysis cycler.

In variations thereof, the disclosed subject includes ones in which controller is configured to run the pump in the first direction to convey medicament from the mixing container to draw one or more concentrates the pump that can run in first and second directions responsively to a first direction, wherein the controller is configured to cause said pump to run in the first direction when pumping said one or more concentrates and water and in second direction opposite direction when pumping through a flow through the peristaltic pump.

According to embodiments, the disclosed subject matter includes an admixing device with a mixing machine with a controller. The mixing machine is configured to engage with a fluid circuit. The fluid circuit has a connector configured for connection to a source of pure water and a connector configured for connecting respectively to at least one source of medicament concentrate. The fluid circuit has a mixing container. The mixing machine further having a pressure sensor configured to engage with the fluid circuit to indicate a pressure of a medicament manifold line that has a connector configured to connect to a plurality of different medicament user device, each requiring a different inlet pressure. The controller is configured to maintain a plurality of pressures that may be applied to the medicament manifold line, a selected one of the plurality of pressures corresponding respectively to one of multiple different medicament user devices.

The embodiments may be modified to form additional embodiments in which the medicament user device includes a peritoneal dialysis cycler.

The embodiments may be modified to form additional embodiments in which the controller is configured to actively control the predefined pressure using a feedback algorithm.

The embodiments may be modified to form additional embodiments in which the mixing machine has a pump actuator and the fluid circuit has a pumping portion configured to engage the pump actuator.

The embodiments may be modified to form additional embodiments in which the pump actuator is a peristaltic pump actuator.

The embodiments may be modified to form additional embodiments in which the mixing machine and the pumping portion is connected between the mixing container and the manifold line.

The embodiments may be modified to form additional embodiments in which the pump actuator runs in a first direction to transfer fluid to the manifold and an opposite separate direction to proportion concentrate and water in the mixing container.

The embodiments may be modified to form additional embodiments in which the manifold and the pressure sensor are directly connected to the pumping portion.

The embodiments may be modified to form additional embodiments in which the pump actuator and pumping portion always pumps fluid into and out of the mixing container.

The embodiments may be modified to form additional embodiments in which the manifold line is connected to valve portions of the fluid circuit and the mixing machine has valve actuators that engage with the valve portions, the fluid circuit having a valve portion engageable with a respective valve actuator for each of the medicament concentrates, one for the medicament user device, one for the one for the source of pure water, one for a drain, and one for the mixing container, wherein a line with the pumping portion that connects the manifold line to the mixing container has no valve portion.

The embodiments may be modified to form additional embodiments in which the mixing container has two lines, both of which connect the mixing container with the manifold line, one connecting to the manifold line through the pumping portion.

The embodiments may be modified to form additional embodiments in which the manifold line is connectable to a drain.

The embodiments may be modified to form additional embodiments in which the pressure sensor is positioned to detect pressure in the manifold line.

According to embodiments, the disclosed subject matter includes a proportioning device with a proportioning machine with a temperature-compensating conductivity sensor, a controller, and pump actuator. a fluid circuit is engageable with the pump actuator. The fluid circuit has connections for a source of water and one or more for one or more medicament concentrates. The fluid circuit has a mixing container. The controller is configured to mix contents of the mixing container at a first time. The proportioning machine controller pump actuator is controlled to sample fluid from the mixing container, to pass the samples from the mixing container through the temperature-compensating conductivity sensor, and to compare conductivities of the samples, wherein the samples are taken at different points in time as the fluid flows from the mixing container. The controller is configured to mix contents of the mixing container a second time if the conductivities differ by a predefined magnitude.

The embodiments may be modified to form additional embodiments in which the mixing container has two lines and the controller mixes contents of the mixing container by flowing fluid into and out of the mixing container by flowing oppositely and continuously through the two lines.

The embodiments may be modified to form additional embodiments in which the pump runs only in a first direction when it proportions medicament concentrate and water in the mixing container.

According to embodiments, the disclosed subject matter includes proportioning device with a proportioning machine with a controller and a pump actuator. A fluid circuit is engageable with the pump actuator. The fluid circuit has a manifold connected to a fluid source and one or more concentrate sources an outlet for a drain and an outlet for diluted concentrate connectable to a predefined cycler. The fluid circuit has a mixing container connected to the pump and the manifold at two locations of the mixing container. The controller is configured to cause the pump to pump fluid into the mixing container while running in a same direction and to pump fluid from the mixing container in an opposite direction into the manifold and out of the mixing container. The proportioning machine is configured pressurize the manifold to predefined pressure for a selected one of a plurality of cyclers, each cycler being different in terms of the inlet pressure range to allow drawing of medicament from the pressurized manifold a pressure that is compatible with the selected one of the plurality of cyclers.

The embodiments may be modified to form additional embodiments in which wherein the pump runs only in a first direction when it proportions medicament concentrate and water in the mixing container.

The embodiments may be modified to form additional embodiments in which the mixing container has two lines connected respectively to an inlet of the mixing container and to an outlet of the mixing container where the inlet and outlet being connect respectively to an inlet and an outlet of the pump.

According to embodiments, the disclosed subject matter includes n admixing system with a consumable fluid circuit with a manifold and a pumping tube segment attached at one end thereof to a mixing container connected by two lines to opposite ends of the pumping tube segment.

The embodiments may be modified to form additional embodiments that include a mixing machine with a controller, valve actuators and a pump actuator engaged with said pumping tube segment the manifold extending away from the pump along a flow single flow path with ports engaged with the valve actuators.

The embodiments may be modified to form additional embodiments in which the ports are connected to a cycler, a drain, one or more mixing containers and a water supply.

The embodiments may be modified to form additional embodiments in which water supply includes one or more filter canisters and housed together with the mixing machine.

The embodiments may be modified to form additional embodiments that include a connector attached to a port of the manifold with a connector connected to a cycler.

The embodiments may be modified to form additional embodiments in which the controller and pump are configured to generate a pressure in said manifold of a predefined magnitude to supply an inlet of the cycler which is one of multiple different cyclers some of which differ in terms of the required pressure range applied at their inlets.

Figure 9:
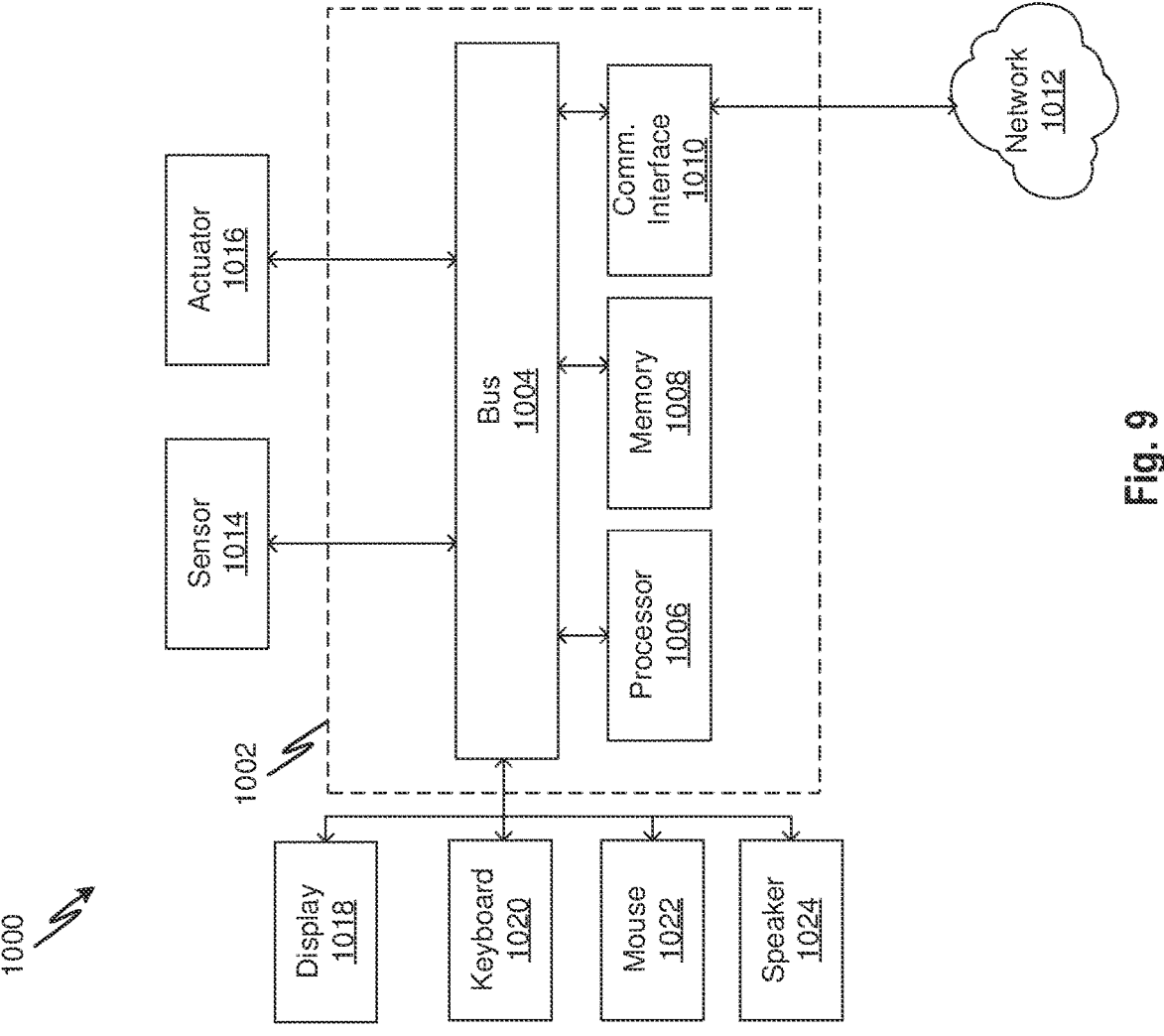
FIG. 9 shows a generic computer system that may describe the functions and elements of a controller as described herein and in accordance with the embodiments of the disclosed subject matter.

FIG. 9 shows a block diagram of an example computer system according to embodiments of the disclosed subject matter. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with one or more sensors 1014 and one or more actuators 1016, each providing respective functionality in accordance with various embodiments disclosed herein, for example, for measuring signals.

It will be appreciated that the modules, processes, systems, and sections described above can be implemented in hardware, hardware programmed by software, software instruction stored on a non-transitory computer readable medium or a combination of the above. For example, a method for providing a medicament to a medicament user can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems of medical devices and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, Medicament Preparation Devices, Methods, and Systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. An admixing device, comprising:
a mixing machine with a controller and a pump actuator;
the mixing machine being configured to engage with a fluid circuit that has a pumping portion configured to engage said pump actuator;
the fluid circuit having a connector configured for connection to a source of pure water and a connector configured for connecting respectively to at least one source of medicament concentrate;

the fluid circuit having a mixing container and a manifold line;

the mixing machine further having a pressure sensor configured to engage with the fluid circuit to indicate a pressure of fluid in the manifold line of the fluid circuit, the manifold line having a connector configured to connect to a selected one of several different medicament user devices;

the controller being configured to, by feedback control, control the pump actuator to maintain a respective target fluid pressure at an inlet to said selected one of several different medicament user devices; and the respective target fluid pressure corresponding respectively to a selected one of multiple different medicament user devices.

2. The device of claim 1, wherein the medicament user device includes a peritoneal dialysis cycler.

3. The device of claim 1, wherein the mixing machine has a pump actuator and said fluid circuit has a pumping portion configured to engage said pump actuator.

4. The device of claim 3, wherein the pump actuator is a peristaltic pump actuator.

5. The device of claim 3, wherein the mixing machine and the pumping portion are connected between said mixing container and said manifold line.

6. The device of claim 5, wherein said pump actuator runs in a first direction to transfer medicament to said manifold line to the medicament user, and an opposite direction to proportion concentrate and pure water in said mixing container.

7. The device of claim 5, wherein the pump actuator is configured to circulate fluid into and out of said mixing container to mix contents of said mixing container.

8. The device of claim 5, wherein said manifold line is connected to valve portions of said fluid circuit and said mixing machine having valve actuators that engage with the valve portions, the fluid circuit having a valve portion engageable with a respective valve actuator for each of said medicament concentrates, one for said medicament user device, one for said source of pure water, one for a drain, and one for said mixing container, wherein a line with said pumping portion that connects the manifold line to said mixing container has no valve portion.

9. The device of claim 8, wherein said mixing container has two lines, both of which connect the mixing container with the manifold line, one connecting to the manifold line through the pumping portion.

10. The device of claim 1, wherein said manifold line is connectable to a drain, and said pressure sensor is positioned to detect pressure in said manifold line.

* * * * *